(12) United States Patent
Tung

(10) Patent No.: US 7,514,068 B2
(45) Date of Patent: Apr. 7, 2009

(54) BIPHENYL-PYRAZOLECARBOXAMIDE COMPOUNDS

(75) Inventor: Roger Tung, Lexington, MA (US)

(73) Assignee: Concert Pharmaceuticals Inc., Lexington, MA (US)

( * ) Notice: Subject to any disclaimer, the term of this patent is extended or adjusted under 35 U.S.C. 154(b) by 93 days.

(21) Appl. No.: 11/521,926

(22) Filed: Sep. 14, 2006

(65) Prior Publication Data

US 2007/0066657 A1 Mar. 22, 2007

Related U.S. Application Data

(60) Provisional application No. 60/735,086, filed on Nov. 8, 2005, provisional application No. 60/717,555, filed on Sep. 14, 2005.

(51) Int. Cl.
*A61K 51/00* (2006.01)
*A61K 31/454* (2006.01)
*C07D 401/02* (2006.01)

(52) U.S. Cl. .................. 424/1.81; 514/326; 546/211

(58) Field of Classification Search .............. 514/326, 514/327, 328, 330, 406, 403; 546/211; 548/364.1, 548/374.1, 377.1, 365.1; 424/1.81
See application file for complete search history.

(56) References Cited

U.S. PATENT DOCUMENTS

| 4,870,095 | A | 9/1989 | Bailey |
| 2007/0276001 | A1* | 11/2007 | Tung .................... 514/326 |
| 2007/0287734 | A1* | 12/2007 | GANT et al. ............. 514/326 |

OTHER PUBLICATIONS

Vippagunta, et al., Crystalline solids, 2001, Advanced Drug Delivery Reviews, 48, pp. 3 and 18.*
Wolff et al., Burger's Medicinal Chemistry and Drug Discovery, 1994, Wiley-Interscience, Fifth Edition, vol. I: Principles and Practice, pp. 975-977.*
Seltzman, et al., Synthesis, Spectral Studies and Tritiation of the Cannabinoid Antagonist SR141716A, 1995, J. Chem. Soc., Chem. Commun., pp. 1549-1550.*
Kushner et al., Pharmacological uses and perspectives of heavy water and deuterated compounds, 1999, Can. J. Physiol. Pharmacol., 77, p. 79.*

* cited by examiner

*Primary Examiner*—Kamal A Saeed
*Assistant Examiner*—Kristin Bianchi
(74) *Attorney, Agent, or Firm*—Edwards Angell Palmer & Dodge LLP; Jeffrey D. Hsi; Mark D. Russett

(57) ABSTRACT

The present invention relates to biphenyl-pyrazole compounds and in particular biphenyl-pyrazolecarboxamides. The invention further provides compositions comprising a compound of this invention and the use of such compositions in methods of treating diseases and conditions beneficially treated by antagonism or inverse agonism of the $CB_1$ receptor, such as obesity, smoking cessation, and normalization of blood lipid composition.

9 Claims, No Drawings

BIPHENYL-PYRAZOLECARBOXAMIDE COMPOUNDS

CROSS-REFERENCE TO RELATED APPLICATIONS

This application claims benefit of U.S. provisional No. 60/717,555, filed Sep. 14, 2005 and U.S. provisional No. 60/735,086, filed Nov. 8, 2005. The contents of these applications are hereby incorporated by reference in their entirety.

TECHNICAL FIELD OF THE INVENTION

The present invention relates to biphenyl-pyrazolecarboxamide compounds. The invention further provides compositions comprising a compound of this invention and the use of such compositions in methods of treating diseases and conditions beneficially treated by antagonism or inverse agonism of the $CB_1$ receptor, such as obesity, smoking cessation, and normalization of blood lipid composition.

BACKGROUND OF THE INVENTION

Biphenyl pyrazoles derivatives with affinity for cannabinoid receptors are described in U.S. Pat. No. 5,624,941 to Sanofi. In that patent, Compound 1, chemically described variously as N-(piperidin-1-yl)-5-(4-chlorophenyl)-1-(2,4-dichlorophenyl)-4-methyl-1H-pyrazole-3-carboxamide; and as N-piperidino-5-(4-chlorophenyl)-1-(2,4-dichlorophenyl)-4-methylpyrazole-3-carboxamide;

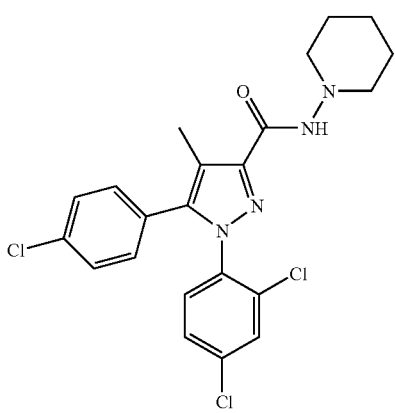

Compound 1 and its pharmaceutically acceptable salts thereof are disclosed as useful antagonists of the cannabinoid $CB_1$ receptor. Compound 1 is a generally highly selective agent, with little activity for the $CB_2$ receptor and a wide variety of other central G-protein coupled receptors. It has also been reported to act as an antagonist of the neurokinin-3 receptor.

It is useful for the treatment or prevention of disorders including obesity, poorly regulated consumption desires, disorders associated with a substance, obesity associated with non-insulin-dependent diabetes, other diseases resulting in patients becoming overweight, bulimia, drug dependency, the desire to consume non-essential food items and the spontaneous appetency for a food item which usually brings pleasure, and neuroinflammatory pathology, particularly such pathology involving demyelinization, viral encephalitis, cerebrovascular accidents, or cranial trauma. See Maruani J and Soubrie P, U.S. Pat. No. 6,344,474 to Sanofi-Synthelabo; and Bourrie B and Casellas P, U.S. Pat. No. 6,642,258 to Sanofi-Synthelabo.

Also disclosed is the use of Compound 1 for the treatment or prevention of diarrhea; obesity in juvenile patients, including in cases of drug-induced obesity; dislipidemia and dislipidemia-associated diseases such as metabolic syndrome; Parkinson's disease; itch; sexual dysfunction; bone disorders; and hepatic diseases including liver fibrosis, alcoholic cirrhosis, chronic viral hepatitis non-alcoholic steatohepatitis, and primary liver cancer. See: Croci T and Manara L, PCT Patent Application WO03018060, Sanofi-Synthelabo Applicant; Benavides J et al., PCT Patent Application WO0185092, Aventis Applicant; Antel J et al., US Patent Application 20050101585, Solvay Applicant; Yasui K et al. PCT Patent Application WO03070277, Shionogi Applicant; Arone M, PCT Patent Application WO03082256, Sanofi-Synthelabo Applicant; Hamilton R S et al., PCT Patent Application WO2004078261, University of Aberdeen Applicant, Arone M, PCT Patent Application, WO2005046689, Sanofi-Aventis Applicant; Lotersztajn S et al., PCT Patent Application WO2005084652, Institut National de la Sante et de la Recherché Medicale and Sanofi-Aventis Applicants.

Compound 1A, chemically described as 5-(4-bromophenyl)-1-(2,4-dichlorophenyl)-4-ethyl-N-(1-piperidinyl)-1H-pyrazole-3-carboxamide, is a derivative of Compound 1 with a favorable pharmacological and bioavailability profile that is currently undergoing clinical evaluation; Thomas B F et al., J. Pharmacol. Exp. Ther. 1998 285: 285; Perio A et al., 14th Symp. Int. Cannabinoid Res. Soc. (Jun 22-Jun 27, Paestum) 2004, Abst 93; Rinaldi-Carmona M et al., J. Phannacol. Exp. Ther. 2004 310: 905.

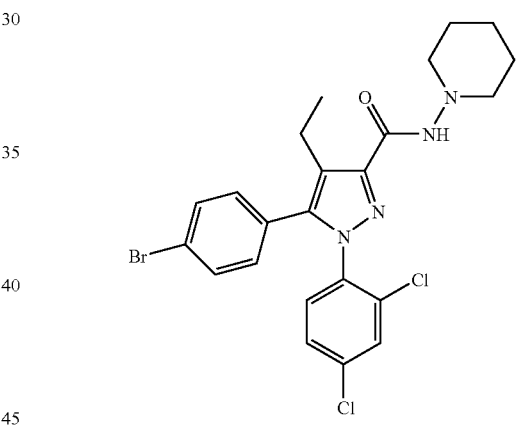

Compound 1A and its pharmacologically acceptable salts and solvates have been disclosed as particularly powerful and selective $CB_1$ antagonists with utility similar to that of Compound 1 as well as good activity in a model system of attention deficit disorder; Arnone M et al., PCT Patent Application WO2005046689, Sanofi-Synthelabo Applicant; Barth F et al., US Patent Application 20040039024, Sanofi-Synthelabo Applicant; Breul T et al., PCT Patent Application WO2005046690, Sanofi-Synthelabo Applicant; Louis, C.; et al. Behav. Pharmacol. 2005 16(Suppl. 1): Abst. A60. Compound 1A is also characterized by a longer duration of action than that of Compound 1 in animal models.

The combination of Compound 1 or 1A with additional agents extends or enhances its utility in the treatment of diabetes and obesity: Cheng P T W et al., U.S. Pat. No. 6,875,782 to Bristol-Myers Squibb, and US Patent Applications 20040063700, 20040063762, and 20050119312 Bristol-Myers Squibb, Applicant.

Additionally disclosed uses for Compound 1 or 1A include methods for its combination with additional appetite suppressants and lipase inhibitors to enhance its anti-obesity effects and to treat or prevent coronary artery disease: Nargund R P et al. US Patent Application 20040122033, Merck & Co. Applicant; Briggs M et al., US Patent Application 20040204472, Pharmacia Applicant; Weber E and Cowley M A et al., US Patent Application 20040254208; Gulve E A and McMahon E G, US Patent Application 20040214804, Pharmacia Applicant; Antel J et al., PCT Patent Application WO2005039579, Solvay Pharma Applicant.

Compounds 1 and 1A have been characterized by in vitro receptor binding studies to be highly selective for the $CB_1$ vs. $CB_2$ receptor and to have little affinity for a wide range of other neurological receptors. Rinaldi-Carmona M et al. FEBS Lett. 1994 350: 240; Thomas B F et al., J. Pharmacol. Exp. Ther. 1998 285: 285; Rinaldi-Carmona M et al., J. Pharmacol. Exp. Ther. 2004 310: 905.

Compounds 1 and 1A also reverse in vivo effects of cannabinoid agonists in rats, including hypothermia, ring immobility, and increased tail flick latency. Rats treated with Compound 1 demonstrate reduced sucrose and ethanol intake and, in obese rats, reduced food intake and body mass, along with greater insulin sensitivity. See e.g. Arnone M et al., Psychopharmacology 1997 132: 104; Trillou C R et al., Am. J. Physiol. Regul. Integr. Comp. Physiol. 2003 284: R345; Perio A et al., 14th Symp. Int. Cannabinoid Res. Soc. (Jun 22-Jun 27, Paestum) 2004, Abst 93.

Compound 1 demonstrates excellent efficacy in reducing weight in obese patients and maintaining weight loss over a period of at least two years. Patients treated with Compound 1 also experienced significant increases in HDL cholesterol and reductions in blood triglycerides, as well as increased insulin sensitivity: Pi-Sunyer FX, Late-Breaking Clinical Trials III, American Heart Association Scientific Sessions 2004, Nov. 7-10, 2004, New Orleans, La.; Heshmati H M et al., Obes. Res. 2001 9(suppl 1):S70; and Van Gaal L F et al., Lancet 2005 365: 1389. Compound 1 is also effective in assisting patients to discontinue tobacco smoking: Dale L et al., Late-Breaking Clinical Trials II. American College of Cardiology Scientific Session 2004, Mar. 7-10, 2004, New Orleans, La.

In reports of these clinical trials Compound 1 was described as having a good safety profile with relatively low increases in serious adverse events across the different dose groups tested. However, it is clearly less well tolerated in higher doses, with the more common side effects including depression, anxiety, and irritability, and in some but not all studies, significant amounts of nausea. Even in a highly motivated Phase III clinical trial population, a considerable number of dose-dependent discontinuations occurred. First year adverse-event associated discontinuations in the RIO-North American trial were 7.2% for placebo versus 9.4% for the weakly efficacious 5 mg dose of Compound 1 and 12.8%, an increase of 77% versus placebo, for the more optimally efficacious 20 mg dose of Compound 1.

It is well known in the art that both efficaciousness and side effects of drugs are commonly concentration-dependent. Increases in tolerability without decreasing efficaciousness, or in some cases while increasing efficaciousness of the drug, can often be accomplished by maintaining blood levels of the drug more consistently between the minimum efficacious concentration and the toxic concentration. See, e.g. Krishnamurthy T N, U.S. Pat. No. 5,215,758 to Euroceltique; Notario G F et al. U.S. Pat. No. 6,872,407 to Abbott Laboratories; Cleary J D et al., Am. J. Health Syst. Pharm. 1999 56 1529; Lyass O et al. Cancer 2000 89: 1037. In certain cases, methods of formulating the drug can help to attain more consistent systemic exposure, but such formulations can be difficult to manufacture, can be expensive due to their proprietary nature, require extensive and costly cross-species in vivo analyses that are not always predictive of human absorption, and can be of limited value if the absorption window for the drug of interest is limited, e.g. to the duodenum, as is often the case (e.g. see Wong P S L et al., U.S. Pat. No. 6,120,803 to Alza and references therein). An alternative approach is to decrease the rate of metabolism of a drug without compromising its beneficial characteristics, if possible, thereby decreasing its rate of clearance. In a drug already given once daily such as Compound 1, increasing its half-life will have the effect of decreasing peak to trough variance when the drug has reached its steady state.

Compound 1 demonstrates relatively few sites of metabolism as demonstrated by rat liver microsome assays. In contrast with a structurally related series of aminoalkylindoles, which are also active cannabinoid receptor ligands, but which are oxidatively metabolized at a number of sites throughout the structure, Compound 1 was found to be subject to hydroxylation only on the pyrazole 3-substituent, i.e. carbon oxidation the N-aminopiperidine ring. See scheme below. Oxidation appears to occur at several sites on the piperidine ring as judged by observation of at least two ring-hydroxylated primary metabolites (designated Ma3 and Ma4 in scheme below) and two dehydro species that presumably resulted either from loss of water from the primary hydroxylated species or potentially by direct dehydrogenation (Ma5 and Ma6 in Scheme I). Further oxidation of these latter metabolites results in the dehydropiperidine alcohols Ma1 and Ma2. Zhang Q et al. Drug Metab. Dispos. 2005 33: 508; Zhang Q et al. Drug Metab. Dispos. 2002 30: 1077; Zhang Q et al. J. Mass Spectrom. 2004 39: 672.

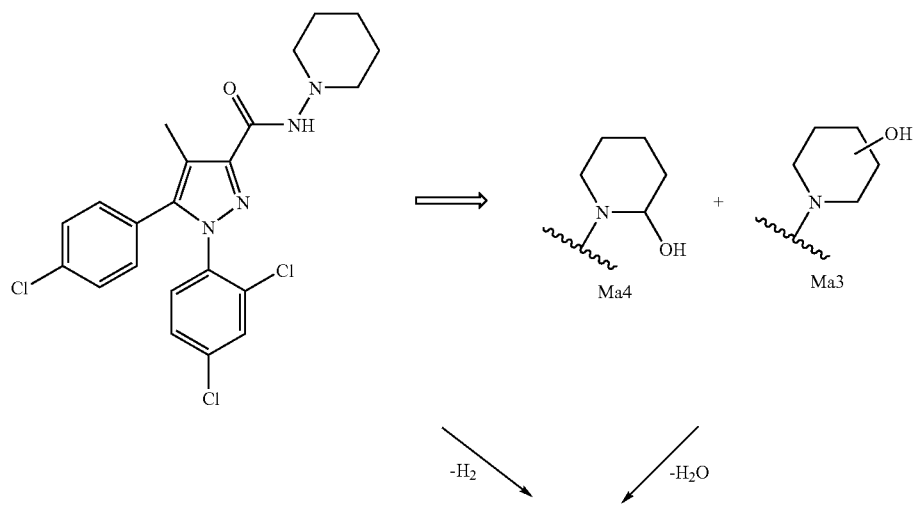

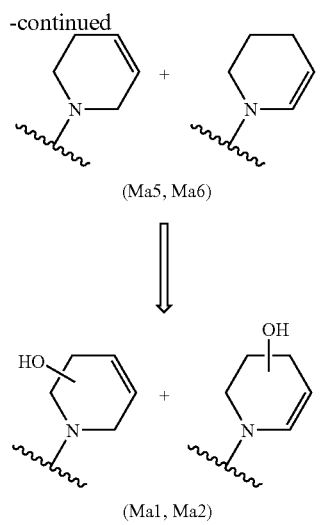

(Ma5, Ma6)

⇓

(Ma1, Ma2)

Since compound 1A also possesses a similar chemical structure and the identical aminopiperidine amide functional group, the piperidine of this compound represents a site of potential metabolism as well.

The biological activity of these metabolites has not been publicly reported to the knowledge of the applicant. However, the effect of replacing the piperidine ring of Compound 1 with a variety of other groups has been published, giving an indication of the structure-activity relationship of $CB_1$ antagonist activity with variations at that portion of the molecule. Short-chain alkane substituents attached to the amide nitrogen in place of a piperidine ring are tolerated with minimal loss of $CB_1$ antagonist activity. The corresponding hydroxyalkanes consistently lose substantial $CB_1$ binding affinity. This suggests that Ma1, Ma2, Ma3 and Ma4 will be less active $CB_1$ antagonists than Compound 1; see e.g. Lan R et al., J. Med. Chem. 1999 42: 769; Francisco E Y et al., J Med. Chem. 2002 45: 2708; Katoch-Rouse R et al., J. Med. Chem. 2003 46: 642. These hydroxylated metabolites also present a likely point for Phase II metabolism such as glucuronide or sulfate conjugation and excretion (see for instance *Enzyme Systems that Metabolize Drugs and Other Xenobiotics* Ionnides C, Ed., 2002, Wiley). Compound 1A shares the pharmacophore of Compound 1 and will have a similar liability for hydroxylated ring metabolites.

Increased polarity and hydrogen bonding capability, particularly hydrogen bond donating ability, are well-correlated with decreased blood-brain barrier penetration (e.g. see Platts J A et al. Eur. J. Med. Chem. 2001 36: 719; Keseru G M and Molnar L, J. Chem. Inf. Comput. Sci. 2001 41: 120; and references therein). Therefore, if the oxidative metabolism of the piperidine ring could be decreased, then for a given dose of Compound 1, a larger amount of active compound would be expected to partition into the brain and reach the central $CB_1$ receptor.

The specific enzymes responsible for the metabolism of Compounds 1 and 1A are, to applicant's knowledge, as yet unreported. However, several important metabolic enzymes responsible for oxidative metabolism, such as cytochrome P450 subtypes 2D6, 2C9, and 2C19, among others, are highly variable between individuals depending on their pharmacogenomic background and can lead to exceedingly large differences in rates of drug metabolism (e.g. Daly A K, Fundam. Clin. Pharmacol. 2003 17: 27; Mancinelli L, AAPS PharmSci 2000 2: E4; Ma MK, Am. J. Health Syst. Pharm. 2002 59: 2061; and references therein). Reducing the susceptibility of a compound to oxidation by these enzymes can decrease the inter-individual pharmacokinetic variability of the drug and enhance its population benefit.

It is therefore desirable to create a compound displaying the beneficial activities of Compounds 1 and 1A, but with a reduced rate of oxidative metabolism.

SUMMARY OF THE INVENTION

The present invention solves the problems set forth above by providing a compound of Formula I:

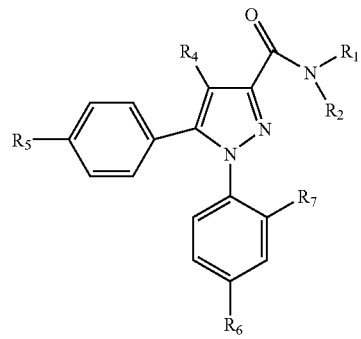

or a salt thereof; or a prodrug or a salt of a prodrug thereof; or a hydrate, solvate and/or polymorph of said compound, salt, prodrug, or prodrug salt, wherein:

each of $R_5$, $R_6$, and $R_7$ are independently selected from halogen or a trifluoromethyl group;

$R_4$ is selected from hydrogen, or a $(C_1-C_3)$-alkyl;

$R_1$ is selected from hydrogen, or a $(C_1-C_3)$-alkyl; and $R_2$ is selected from a $(C_1-C_6)$-alkyl; a non-aromatic $(C_3-C_{15})$ carbocyclic radical; an amino group monosubstituted or disubstitued with an independently selected $(C_1-C_4)$-alkyl; or a saturated 5- to 8-membered heterocyclic radical optionally substituted with a $(C_1-C_3)$-alkyl or a hydroxyl group;

or $R_1$ and $R_2$, together with the nitrogen atom to which they are bonded, form a saturated 5- to 8-membered heterocyclic radical;

wherein:

each alkyl, each non-aromatic $(C_3-C_{15})$ carbocyclic radical and each saturated 5- to 8-membered heterocyclic radical is optionally deuterated and optionally fluorinated;

at least one of $R_1$, $R_2$ and R4 comprises a deuterium atom; or at least one of $R_1$, $R_2$ and R4 comprises a difluorinated carbon atom;

each independent hydrogen atom not present in $R_1$, $R_2$ or R4 is optionally replaced with deuterium; and each independent carbon atom is optionally replaced with $^{13}C$.

In one preferred embodiment, the compound is a compound of Formula II:

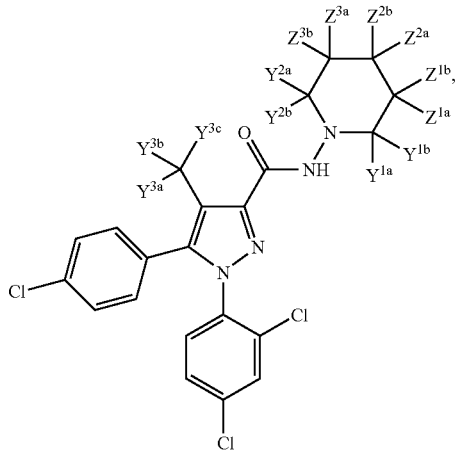

(II)

or a compound of Formula IIA:

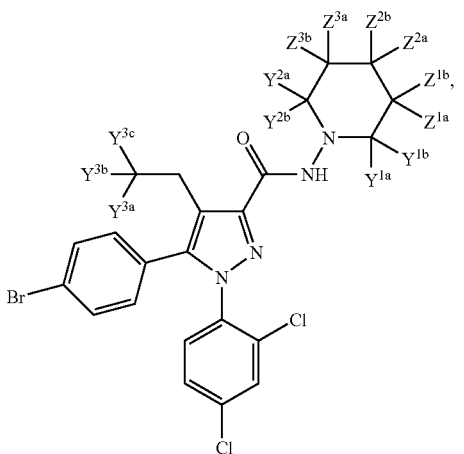

(IIA)

or a compound of Formula IIB:

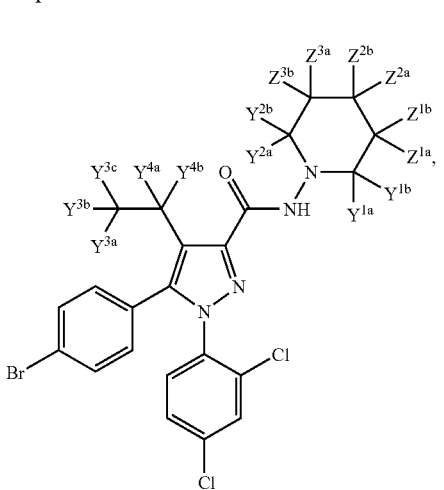

(IIB)

or a salt thereof; or a prodrug or a salt of a prodrug thereof; or a hydrate, solvate and/or polymorph of said compound, salt, prodrug, or prodrug salt; wherein:

each Y is independently selected from deuterium or hydrogen;

each Z is independently selected from deuterium, hydrogen, or fluorine;

at least one Y or one Z is deuterium, or at least two Z are fluorine;

each hydrogen is independently and optionally replaced with deuterium; and each carbon is independently and optionally replaced with $^{13}C$.

The compounds of this invention demonstrate advantageous biopharmaceutical properties over compounds having identical structure except for the presence of deuterium and/or fluorine. These properties include reduced rates of hepatic oxidative metabolism due to the presence of fluorine or replacement of hydrogen by deuterium. This property results in enhanced pharmacological effects and the potential for reduced dosing of compounds of the invention to achieve similar or superior medical effects as compared to dosing of a similar quantity of undeuterated and/or underfluorinated or unfluorinated compounds of otherwise identical structure. This beneficially reduces peak concentration-associated adverse events. In particular, a compound of Formulae II, or IIA or IIB are believed to be superior to Compound 1 or Compound 1A, respectively. A compound of this invention, and specifically a compound of Formula II, IIA, or IIB also displays the ability to penetrate the blood-brain barrier and thus reach its target brain receptor.

The compounds of this invention and compositions comprising them, are useful to reduce or ameliorate severity, duration, or progression, or enhance function compromised by, a disorder beneficially treated by antagonism or inverse agonism of the $CB_1$ receptor. In one embodiment, the invention provides a method of preventing or reducing the severity of a condition selected from obesity, alcoholism, a blood lipid disorder, substance abuse, a neuroinflammatory pathology, an eating disorder or for enhancing smoking cessation, said method comprising the step of administering to a subject suffering from said condition or attempting to stop smoking a composition comprising a compound of Formula I and a pharmaceutically acceptable carrier.

The compounds and compositions of this invention are also useful as analytical reagents for determining the concentration of the corresponding undeuterated and/or unfluorinated or underfluroinated compound. In a preferred embodiment, a compound of Formula II, or IIA or IIB is used to determine the concentration of Compound 1 or Compound 1A, respectively, in a solution.

The term "corresponding undeuterated compound" refers to a compound having identical chemical structure as a reference compound except that all hydrogen and all carbon atoms are present at their natural isotopic abundance percentages. The term "corresponding unfluorinated or underfluorinated compound" refers to a compound having identical chemical structure as a reference compound except lacking a di- or tri-fluorinated carbon atom. "Compound 1" and "Compound 1A" as used herein each refers to a compound whose structure is shown above in the Background of the Invention, wherein all hydrogen and all carbon atoms are present at their natural isotopic abundance percentages. It is recognized that some variation of natural isotopic abundance occurs depending upon the origin of chemical materials. The concentration of naturally abundant stable hydrogen and carbon isotopes, even given this variation, is small and immaterial with respect to the degree of stable isotopic substitution of compounds of this invention. See for instance Wada E and Hanba Y, Seikagaku 1994 66: 15; Ganes L Z et al. Comp. Biochem. Physiol. A Mol. Integr. Physiol. 1998 119: 725.

Fluorination has unpredictable effects on the biological activity of compounds in which it is incorporated in place of hydrogen; see e.g. Smart B E, J. Fluorine Chem. 2001 109: 3 and Ismail F M D, J. Fluorine Chem. 2002 118: 27. This is due to the exceedingly high electronegativity of fluorine relative to hydrogen, and the significantly larger van der Waals volume of fluorine in a C—F bond relative to hydrogen in a C—H bond.

Surprisingly, the fluorinated derivatives of this invention are highly active $CB_1$ receptor antagonists that both retain excellent selectivity with respect to the $CB_2$ receptor and significantly alter oxidative metabolism as compared to the corresponding unfluorinated or under-fluorinated compound. This is particularly true in the case of the piperidine ring in compounds of Formula II, IIA or IIB.

Incorporation of deuterium in place of hydrogen is known in certain instances to have significant effects on the physiological and pharmacological activities of the substituted compound. For instance, N-nitrosamines substituted with deuterium can display increased, decreased, or unchanged carcinogenicity depending on where in the compound hydrogen is replaced with deuterium and on the identity of the compound to which substitutions are made (Lijinsky W et al. Food Cosmet Toxicol. 1982 20: 393; Lijinsky W et al. JCNI 1982 69: 1127). Similarly, both increases and decreases in bacterial mutagenicity of deuterium-substituted aza-amino acids are known, depending on the identity of the amino acid derivative and position of substitution (Mangold J B et al. Mutation Res. 1994 308: 33). Reduced hepatotoxicity of certain deuterium-substituted compounds is known (Gordon W P et al. Drug Metab. Dispos.1987 15: 589; Thompson D C et al. Chem. Biol. Interact. 1996 101: 1). Deuterium substitution can affect compound's odors (Turin L, Chem. Senses 1996 21: 773) and plasma protein binding (Echmann M L et al. J. Pharm. Sci. 1962 51: 66; Cherrah Y. et al. Biomed. Environm. Mass Spectrom. 1987 14: 653; Cherrah Y. et al. Biochem. Pharmacol. 1988 37: 1311). Changes in the biodistribution and clearance of certain deuterium-substituted compounds suggests changes in their recognition by active transport mechanisms (Zello G A et al. Metabolism 1994 43: 487; Gately S J et al. J. Nucl. Med. 1986 27: 388; Wade D, Chem. Biol. Interact. 1999 117: 191).

Replacement of hydrogen with deuterium at sites subject to oxidative metabolism by, for instance, heme proteins such as cytochrome P450 and peroxidase enzymes, and monoamine oxidases, is known in certain, but not all, cases to produce a significant reduction in the rate of metabolism due to the primary isotope effect of breaking the C—$^1$H versus C—$^2$H bond (see, e.g., Guengerich F P et al. J. Biol. Chem. 2002 277: 33711; Kraus, J A and Guengerich, F P, J. Biol. Chem. 2005 280: 19496; Mitchell K H et al., Proc. Natl. Acad. Sci. USA 2003 109: 3784; Nelson SD and Trager WF, Drug Metab. Dispos. 2003 31: 1481; Hall L R and Hanzlik, R P J. Biol. Chem. 1990 265: 12349; Okazaki O. and Guengerich F P J. Biol. Chem. 268, 1546; Iwamura S et al. J. Pharmacobio-Dyn. 1987 10: 229; Yu P H and Davis B A, Int. J. Biochem. 1988 20: 1197; Yu P H et al., Biochem. Pharmacol. 1986 35: 1027.). If the C—H bond breaking step is rate-limiting a substantial isotope effect can be observed. If other steps determine the overall rate of reaction, the isotope effect may be insubstantial. In cases where a rate limiting step of a reaction involves rehybridization of the attached carbon from sp2 to sp3, deuterium substitution often creates a negative isotope effect, speeding up the reaction rate. Introducing deuterium into a compound at a site subject to enzymatic oxidation does not predictably produce a significant pharmacokinetic change. See for instance Perel J M et al., J. Med. Chem. 1967 10: 371; Mamada K et al. Drug Metab. Dispos. 1986 14: 509; Streeter A J et al. Arch. Toxicol. 1990 64: 109; Taylor I W, Biochem. Pharmacol. 1983 32: 641; Morgan D S et al., Int. Arch. Occup. Environ. Health 1993 65(1 Suppl.): S139.

Although incorporation of deuterium into specific organic compounds can change their pharmacological properties, general exposure to and incorporation of deuterium is safe within levels potentially achieved by use of compounds of this invention as medicaments. For instance, the weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp.125-134.). These authors report a clinical protocol in their practice involving oral administration of up to 1 liter per day of deuterated water ($D_2O$) for up to 5 days, followed by intravenous administration of 4 liters of deuterated water prior to radiation procedures; this deuterated water is readily incorporated throughout the body beyond the fluid compartment, including in glucose and glycogen, fats, and cholesterol and thus cell walls (e.g. see Diabetes Metab. 1997 23: 251). In a 70 kg human male, 15% replacement of the hydrogen in the fluid compartment with deuterium corresponds to incorporation of approximately 1 kg of deuterium or the equivalent of approximately 5 kg of deuterated water. These quantities are orders of magnitude beyond the conceived level of administration of any of the deuterium-containing compounds of this invention.

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The deuterium-substituted compounds of this invention retain their ability to bind to their enzymatic target. This is because such binding is primarily dependent upon non-covalent binding between the enzyme and the inhibitor. Non-covalent binding may be impacted both positively and negatively by isotopic substitution, depending on the specific substitution involved. Major factors contributing to the non-covalent recognition of small molecules by proteins and the binding strength between them include: Van der Waals forces, hydrogen bonds, ionic bonds, molecular reorganization, desolvation energy of the small molecule, hydrophobic interactions and, in certain instances, displacement energy for pre-existing bound ligands. See, for instance, Goodman & Gilman's The Pharmacological Basis of Therapeutics, Tenth Edition, Hardman J G and Limbird L E, eds. McGraw-Hill, 2001. Any negative effects that a heavy atom in a compound of this invention may have on that compound's highly optimized non-covalent binding to the $CB_1$ receptor will be relatively minor.

The deuterated and $^{13}C$-containing compounds of this invention possess molecular topology that is very similar to their corresponding undeuterated compounds, since exchange of deuterium for hydrogen does not alter molecular shape; and exchange of $^{13}C$ for $^{12}C$ is conformationally neutral (Holtzer M E et al., Biophys. J. 2001 80: 939). Deuterium replacement does cause a slight decrease in Van der Waals radius (Wade D, Chem. Biol. Interact. 1999 117: 191); but applicant believes that such decrease will not greatly reduce binding affinity between the molecule and the $CB_1$ receptor. Furthermore, the smaller size of the deuterated compounds of this invention prevents their being involved in new undesirable steric clashes with the binding protein relative to the corresponding undeuterated compound. Neither deuterium nor $^{13}C$ atoms, if present in the compounds of this invention, contribute significantly to hydrogen bonding or ionic interactions with the protein receptors. This is because the major hydrogen bond and ionic interactions formed by these compounds with the $CB_1$ receptor are mediated by their nitrogens and carbonyl oxygen, with the amide NH acting as a hydrogen bond donor. Any deuterium atoms attached to the amide nitrogen will be rapidly exchanged with bulk solvent protons under physiological conditions. Protein reorganization or side chain movement will be identical between a compound of this invention and its corresponding undeuterated and/or unfluorinated or under-fluorinated compound. Desolvation energy of a compound of this invention will be equivalent to or less than that of such a corresponding compound resulting in neutral or increased binding affinity for the receptor; Turowski M et al., J. Am. Chem. Soc. 2003 125: 13836. The replacement of $^{13}C$ in place of $^{12}C$ in compounds of this invention will have no practical effect on desolation.

Thus, a compound of this invention advantageously retains substantial binding to the $CB_1$ receptor and selectivity for that isoform relative to $CB_2$.

DETAILED DESCRIPTION OF THE INVENTION

In one embodiment, the present invention provides a compound of Formula I:

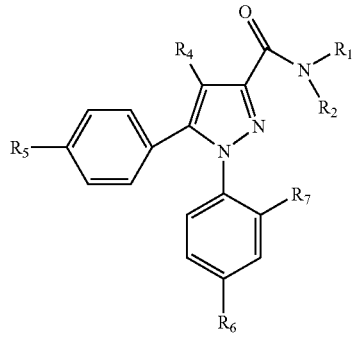

or a salt thereof; or a prodrug or a salt of a prodrug thereof; or a hydrate, solvate and/or polymorph of said compound, salt, prodrug, or prodrug salt, wherein:

each of $R_5$, $R_6$, and $R_7$ are independently selected from halogen or a trifluoromethyl group;

$R_4$ is selected from hydrogen, or a $(C_1-C_3)$-alkyl;

$R_1$ is selected from hydrogen, or a $(C_1-C_3)$-alkyl; and $R_2$ is selected from a $(C_1-C_6)$-alkyl; a non-aromatic $(C_3-C_{15})$ carbocyclic radical; an amino group monosubstituted or disubstitued with an independently selected $(C_1-C_4)$-alkyl; or a saturated 5- to 8-membered heterocyclic radical optionally substituted with a $(C_1-C_3)$-alkyl or a hydroxyl group;

or $R_1$ and $R_2$, together with the nitrogen atom to which they are bonded, form a saturated 5- to 8-membered heterocyclic radical;

wherein:

each alkyl, each non-aromatic $(C_3-C_{15})$ carbocyclic radical and each saturated 5- to 8-membered heterocyclic radical is optionally deuterated and optionally fluorinated;

at least one of $R_1$, $R_2$ and R4 comprises a deuterium atom; or at least one of $R_1$, $R_2$ and R4 comprises a difluorinated carbon atom;

each independent hydrogen atom not present in $R_1$, $R_2$ or R4 is optionally replaced with deuterium; and each independent carbon atom is optionally replaced with $^{13}C$.

In one preferred embodiment, each of $R_5$, $R_6$ and $R_7$ is independently selected from a chlorine atom or a bromine atom. More preferred is when $R_6$ and $R_7$ are simultaneously chlorine atoms.

In yet another preferred embodiment, $R_4$ is selected from —$CH_2$—$C(Y^{3a})(Y^{3b})(Y^{3c})$, —$C(Y^{4a})(Y^{4b})$—$C(Y^{3a})(Y^{3b})$ $(Y^{3c})$ or —$C(Y^{3a})(Y^{3b})(Y^{3c})$, wherein each Y is independently selected from hydrogen, fluorine or deuterium.

In another preferred embodiment $R_1$ is selected from hydrogen or methyl; and $R_2$ is selected from a saturated 5- to 8-membered heterocyclic radical selected from 1-pyrrolidinyl, 1-piperidinyl, 1-hexahydroazepinyl, 4-morpholinyl or 4-thiomorpholinyl; a non-aromatic $(C_3-C_{15})$ carbocyclic radical; or a $(C_1-C_6)$-alkyl.

In another preferred embodiment, the compound is selected from a compound of Formula II:

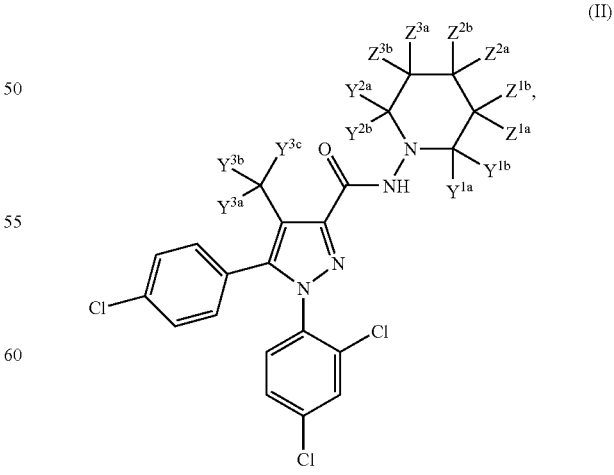

or a compound of Formula IIA:

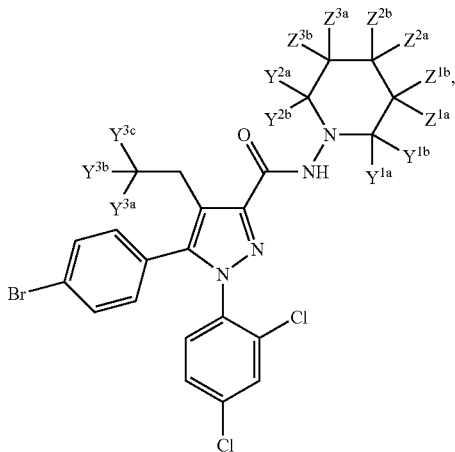

(IIA)

or a compound of Formula IIB:

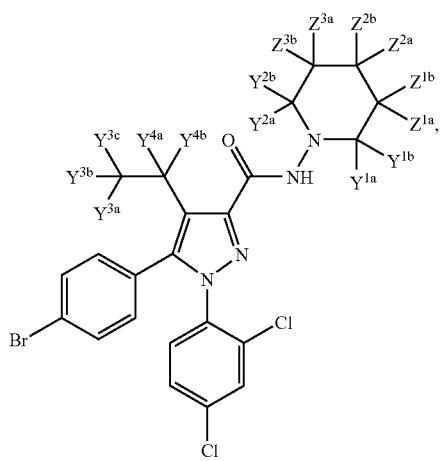

(IIB)

or a salt thereo; or a prodrug or a salt of a prodrug thereof; or a hydrate, solvate and/or polymorph of said compound, salt, prodrug, or prodrug salt; wherein:

each Y is independently selected from deuterium or hydrogen;

each Z is independently selected from deuterium, hydrogen, or fluorine;

at least one Y or one Z is deuterium, or at least two Z on the same carbon atom are fluorine;

each independent hydrogen at a position other than Y or Z is optionally replaced with deuterium; and each independent carbon is optionally replaced with $^{13}C$ According to one preferred embodiment, at least one Y or Z is deuterium.

According to another embodiment, each of $Y^{3a}$, $Y^{3b}$ and $Y^{3c}$ is the same.

In yet another preferred embodiment, each of $Y^{4a}$ and $Y^{4b}$ is the same. More preferably, each of $Y^{3a}$, $Y^{3b}$, $Y^{3c}$, $Y^{4a}$, and $Y^{4b}$ is the same.

In another preferred embodiment, each of $Y^{1a}$, $Y^{1b}$, $Y^{2a}$, and $Y^{2b}$ are simultaneously deuterium.

In yet another preferred embodiment, at least one Y or one Z is deuterium; and at least one Z is fluorine.

According to yet another embodiment, each of $Y^{1a}$, $Y^{1b}$, $Y^{2a}$, $Y^{2b}$, $Z^{1a}$, $Z^{1b}$, $Z^{2b}$, $Z^{3a}$ and $Z^{3b}$ is simultaneously deuterium; and $Z^{2a}$ is hydrogen.

In another preferred embodiment, no hydrogen at a position other than Y or Z is replaced with deuterium. More preferably, in addition, no $^{12}C$ is replaced with $^{13}C$.

A more preferred embodiment of this invention is, independently, a compound of any one of the compound classes numbered 2-49 in Table I, below. In this table for each compound class, any Y and Z not otherwise designated is an irreplaceable hydrogen, present at its naturally abundant isotopic state. Each other hydrogen atom present in a compound of each designated class is optionally replaced with deuterium. Each $^{12}C$ atoms present in a compound of each designated class is optionally replaced with $^{13}C$.

TABLE 1

| Preferred Compound Classes of the Invention |
|---|

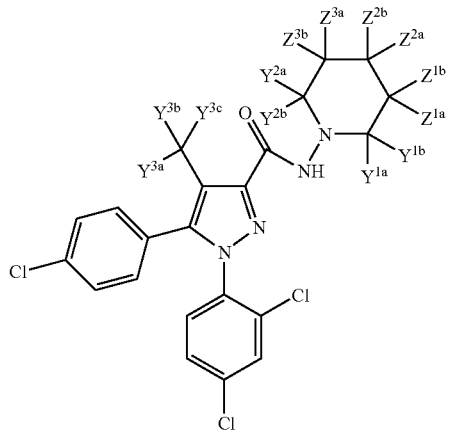

(II)

TABLE 1-continued

Preferred Compound Classes of the Invention

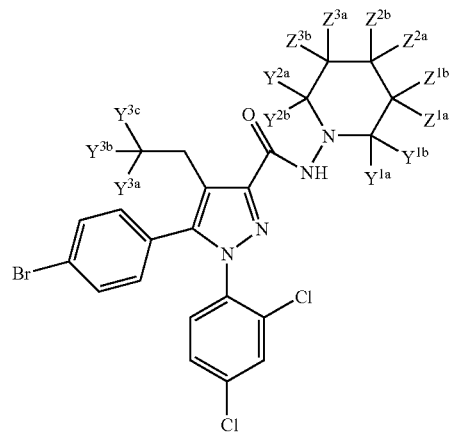

(IIA)

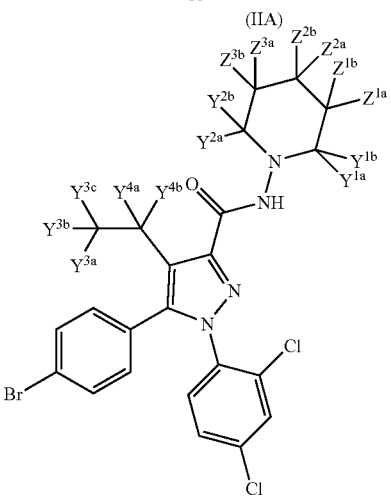

(IIB)

| Compound Class | $Y^{1a}$ | $Y^{1b}$ | $Y^{2a}$ | $Y^{2b}$ | $Y^{3a}$ | $Y^{3b}$ | $Y^{3c}$ | $Z^{1a}$ | $Z^{1b}$ | $Z^{2a}$ | $Z^{2b}$ | $Z^{3a}$ | $Z^{3b}$ | $Y^{4a}$ | $Y^{4b}$ | Formula |
|---|---|---|---|---|---|---|---|---|---|---|---|---|---|---|---|---|
| 2 | D | | D | | | | | D | D | D | D | D | | | | II |
| 3 | D | | D | | D | D | D | D | D | D | D | D | | | | II |
| 4 | D | D | D | D | | | | | | | | | | | | II |
| 5 | D | D | D | D | D | D | D | | | | | | | | | II |
| 6 | | | | | D | D | D | | | | | | | | | II |
| 7 | D | D | D | D | | | | D | D | D | D | D | | | | II |
| 8 | D | D | D | D | D | D | D | D | D | D | D | D | | | | II |
| 9 | D | D | D | D | | | | D | D | D | D | D | D | | | II |
| 10 | D | D | D | D | D | D | D | D | D | D | D | D | D | | | II |
| 11 | D | D | D | D | | | | | | F | | | | | | II |
| 12 | | | | | D | D | D | | | F | | | | | | II |
| 13 | D | D | D | D | D | D | D | | | F | | | | | | II |
| 14 | | | | | | | | | | F | F | | | | | II |
| 15 | D | D | D | D | | | | | | F | F | | | | | II |
| 16 | | | | | D | D | D | | | F | F | | | | | II |
| 17 | D | D | D | D | D | D | D | | | F | F | | | | | II |
| 18 | | | | | | | | F | F | | | F | F | | | II |
| 19 | D | D | D | D | | | | F | F | | | F | F | II | | |
| 20 | | | | | D | D | D | F | F | | | F | F | | | II |
| 21 | D | D | D | D | D | D | D | F | F | | | F | F | | | II |
| 22 | | | | | | | | F | F | F | F | F | F | | | II |
| 23 | D | D | D | D | | | | F | F | F | F | F | F | | II | |
| 24 | | | | | D | D | D | F | F | F | F | F | F | | | II |
| 25 | D | D | D | D | | | | F | F | D | D | F | F | | | II |
| 26 | D | D | D | D | D | D | D | F | F | D | D | F | F | | | II |
| 27 | D | D | D | D | | | | F | | | | F | | | | II |
| 28 | D | | D | | | | | D | D | D | D | | | | | IIA |

TABLE 1-continued

Preferred Compound Classes of the Invention

| # | Y1a | Y1b | Y2a | Y2b | Y3a | Y3b | Y3c | Y4a | Y4b | Z1a | Z1b | Z2a | Z2b | Z3a | Z3b | Formula |
|---|---|---|---|---|---|---|---|---|---|---|---|---|---|---|---|---|
| 29 | D |  | D |  | D | D | D | D | D | D | D | D |  |  |  | IIA |
| 30 | D | D | D | D |  |  |  |  |  |  |  |  |  |  |  | IIA |
| 31 | D | D | D | D | D | D | D |  |  |  |  |  |  |  |  | IIA |
| 32 | D | D | D | D |  |  |  | D | D | D | D | D |  |  |  | IIA |
| 33 | D | D | D | D | D | D | D | D | D | D | D | D |  |  |  | IIA |
| 34 | D | D | D | D |  |  |  | D | D | D | D | D | D |  |  | IIA |
| 35 | D | D | D | D | D | D | D | D | D | D | D | D | D |  |  | IIA |
| 36 | D | D | D | D |  |  |  |  |  | F |  |  |  |  |  | IIA |
| 37 |  |  |  |  | D | D | D |  |  |  |  |  |  |  |  | IIA |
| 38 |  |  |  |  | D | D | D |  |  | F |  |  |  |  |  | IIA |
| 38 | D | D | D | D | D | D | D |  |  | F |  |  |  |  |  | IIA |
| 39 |  |  |  |  |  |  |  |  |  | F | F |  |  |  |  | IIA |
| 40 | D | D | D | D |  |  |  |  |  | F | F |  |  |  |  | IIA |
| 41 |  |  |  |  | D | D | D |  |  | F | F |  |  |  |  | IIA |
| 42 | D | D | D | D | D | D | D |  |  | F | F |  |  |  |  | IIA |
| 43 |  |  |  |  |  |  |  | F | F |  |  | F | F |  |  | IIA |
| 44 | D | D | D | D |  |  |  | F | F |  |  | F | F |  |  | IIA |
| 45 |  |  |  |  | D | D | D | F | F |  |  | F | F |  |  | IIA |
| 46 | D | D | D | D | D | D | D | F | F |  |  | F | F |  |  | IIA |
| 47 | D | D | D | D |  |  |  | F | F | D | D | F | F |  |  | IIA |
| 48 |  |  |  |  | D | D | D | F | F | D | D | F | F |  |  | IIA |
| 49 | D | D | D | D |  |  |  | F | F | D | D | F | F |  |  | IIA |
| 50 | D |  | D |  | D | D | D | D | D | D | D |  |  | D | D | IIB |
| 51 | D | D | D | D | D | D | D |  |  |  |  |  |  | D | D | IIB |
| 52 |  |  |  |  | D | D | D |  |  |  |  |  |  | D | D | IIB |
| 53 | D | D | D | D | D | D | D | D | D | D | D | D |  | D | D | IIB |
| 54 | D | D | D | D | D | D | D | D | D | D | D | D | D | D | D | IIB |
| 55 |  |  |  |  | D | D | D |  |  | F |  |  |  | D | D | IIB |
| 56 | D | D | D | D | D | D | D |  |  | F |  |  |  | D | D | IIB |
| 57 |  |  |  |  | D | D | D |  |  | F | F |  |  | D | D | IIB |
| 58 | D | D | D | D | D | D | D |  |  | F | F |  |  | D | D | IIB |
| 59 |  |  |  |  | D | D | D | F | F |  |  | F | F | D | D | IIB |
| 60 | D | D | D | D | D | D | D | F | F |  |  | F | F | D | D | IIB |
| 61 |  |  |  |  | D | D | D | F | F | F | F | F | F | D | D | IIB |

Even more preferred is a compound from those compound classes above, wherein at least one Y or one Z is deuterium. Most preferred is a compound selected from any one of compound classes 4, 5, 6, 11, 12, 15, 16, 30, 37, 38, 40, 41, 51, 52, 55, or 57.

In each of compound classes 2 through 49 in Table 1, above, and in the more preferred compound classes referred to above, it is preferred that no hydrogen atoms be replaced with deuterium other than any Y or Z designated as deuterium in the table. Specific embodiments of the compounds herein are those exemplified in the Tables herein wherein no other hydrogen atoms are replaced with deuterium (e.g., where the only deuterium atoms in the molecule are Y or Z atoms designated as deuterium in the table). Even more preferred is that in addition, no $^{12}C$ atoms present in any compound of compound classes 2 through 49 be replaced with $^{13}C$.

The terms "compound of Formula 1," "compound of Formula II," and "compound of Formula IIA" as used herein, are intended to include salts, prodrugs and prodrug salts of said compound. The term also includes any solvates, hydrates and polymorphs of any of the foregoing.

A preferred salt of a compound of Formula II or Formula IIA is one wherein the counterion of the salt is pharmaceutically acceptable. Even more preferred is wherein the salts and solvates are selected from the group consisting of the hydrochloride or its solvate with ethanol, the methanesulfonate or its hemisolvate with acetone, the hemifumarate, the hydrogensulfate, the paratoluenesulfonate and the dihydrogenphosphate.

Throughout this specification, reference to "each Y" includes, independently, all "Y" groups ($Y^{1a}$, $Y^{1b}$, $Y^{2a}$, $Y^{2b}$, $Y^{3a}$, $Y^{3b}$, $Y^{3c}$, $Y^{4a}$, $Y^{4b}$), and reference to "each Z" includes, independently, all "Z" groups ($Z^{1a}$, $Z^{1b}$, $Z^{2a}$, $Z^{2b}$, $Z^{3a}$, and $Z^{3b}$) where applicable.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines.

A prodrug salt is a compound formed between an acid and a basic group of the prodrug, such as an amino functional group, or a base and an acidic group of the prodrug, such as a carboxyl functional group. In a preferred embodiment, the prodrug salt is a pharmaceutically acceptable salt. According to another preferred embodiment, the counterion to the saltable prodrug of the compound of Formula I is pharmaceutically acceptable. Pharmaceutically acceptable counterions include, for instance, those acids and bases noted herein as being suitable to form pharmaceutically acceptable salts.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfiric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

The term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

Another aspect of the invention is a compound of the invention for use in the treatment or prevention in a subject of a disease, disorder or symptom thereof delineated herein.

Another aspect of the invention is the use of a compound of the invention in the manufacture of a medicament for treatment or prevention in a subject of a disease, disorder or symptom thereof delineated herein.

The compounds of the invention may be synthesized by well-known techniques. The starting materials and certain intermediates used in the synthesis of the compounds of this invention are available from commercial sources or may themselves be synthesized using reagents and techniques known in the art, including those synthesis schemes delineated herein. See, for instance, European Patent EP 0656354 to Sanofi; Barth F et al. U.S. Pat. No. 5,462,960 to Sanofi; Barth F et al., U.S. Pat. No. 5,624,941 to Sanofi; Dutta A K et al., Med. Chem. Res. 1994 5: 54; Seltzmann H H et al., J. Chem. Soc. Chem. Commun. 1995 15: 1549; Lan R et al., J. Med. Chem. 1999 42 769; and Katoch-Rouse R et al. J. Med. Chem. 2003 46: 642. Each of these documents is incorporated herein by reference
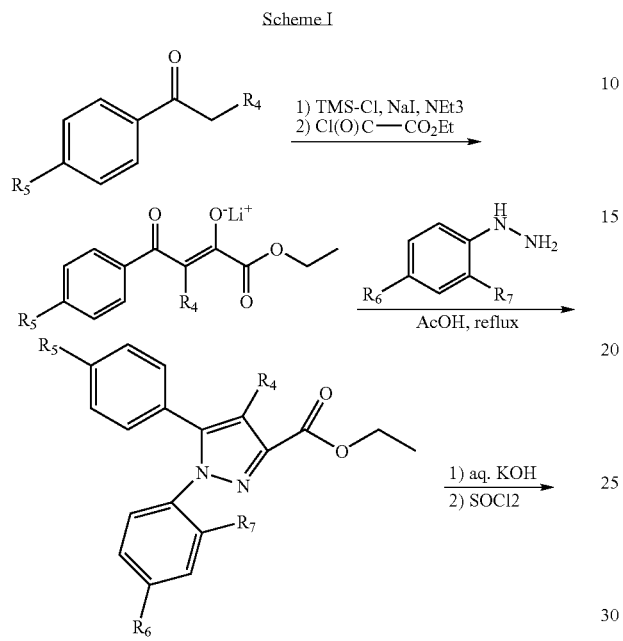
Scheme I
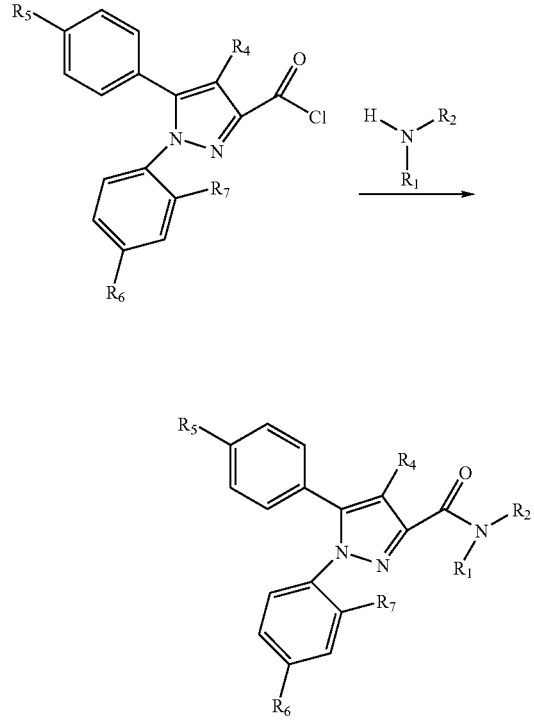
Scheme II
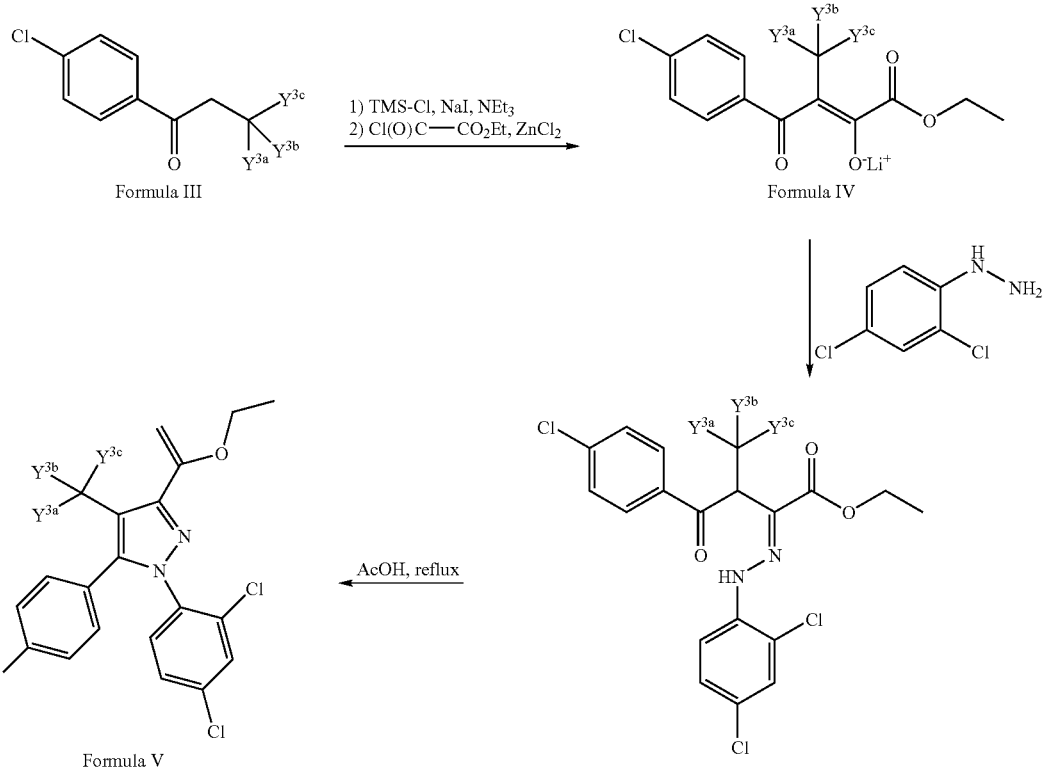

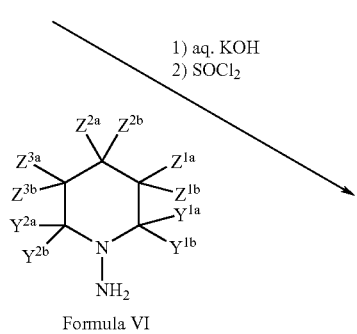

Formula VI

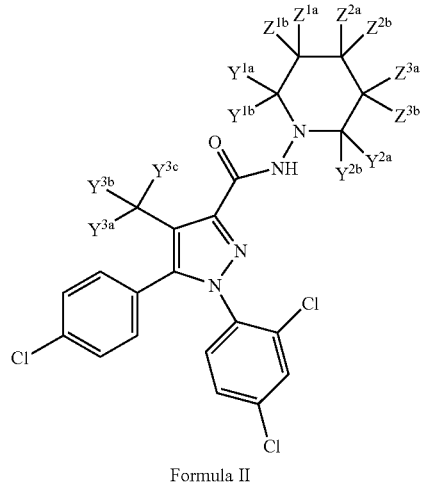

Formula II

One convenient method for producing a compound of Formula I is illustrated in Scheme 1. The same general scheme is used to produce a compound of Formula II as is graphically illustrated in scheme II. Variations in reactants and reaction conditions are described the above-cited synthetic references, and others will be evident to those of ordinary skill in organic synthesis and process chemistry development.

Compounds of Formula III can be readily synthesized, for instance, by metallation of 1-bromo-4-chlorobenzene and acylation with a suitable propionate electrophile, e.g. the Weinreb amides of the commercially available 3,3,3-trideuteropropionic acid or perdeuteropropionic acid, or other isotopologues known in the art (see e.g. Nahm S and Weinreb S M, Tetrahedron Lett. 1981 22: 3815). Acylation with diethyl oxalate, hydrazone formation and cyclization with loss of water produces esters of Formula V. Saponification of the ester group, formation of the acid chloride and reaction with 1-aminopiperidine derivatives of formula VI then give the compounds of Formula II Deuterium-containing compounds of formula VI are available, for instance, by reduction of the corresponding N-nitroso-deuteropiperidines of formula VIII by means known in the art, for instance, see Rybczynski W et al. U.S. Pat. No. 5,510,489 to Cassella, and references therein. These N-nitrosopiperidines may be obtained by nitrosation of the N-unsubstituted piperidine derivatives of formula VI, for instance, by reaction with nitrous acid (e.g. formed in situ from sodium nitrite and aqueous acid) or other known nitrosating reagents. See for instance Zolfigol M A et al., Bull. Korean Chem. Soc. 2003 24: 639, and references cited therein.

Scheme III illustrates this transformation. In a convenient process, nitrosation of the piperidine derivative can be carried out using sodium nitrite in acetic acid and reduction of the resulting nitrosamine effected in the same vessel by addition of metallic zinc. Other methods of N-amination of piperidine and other secondary amine-bearing heterocycles are also known in the art; see for instance Hynes J Jr. et al. J. Org. Chem. 2004 69: 1368 and references therein.

Scheme III

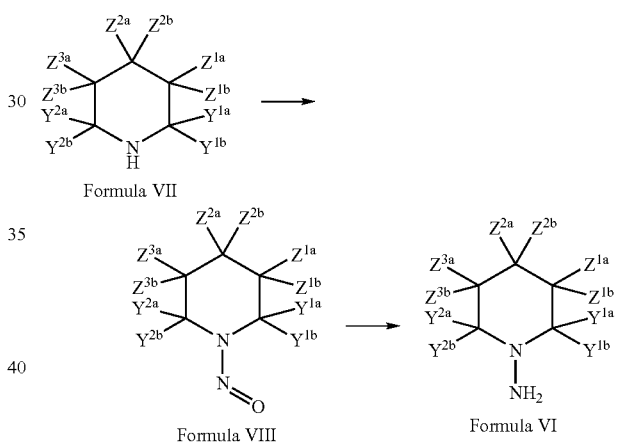

Formula VII

Formula VIII

Formula VI

Piperidine derivatives of formula VII are available by numerous means known in the art, several of which are illustrated in Scheme IV. Numerous deuterated piperidine analogs are known: see, e.g. Coumbarides G S et al. J. Label. Cmpd. Radiopharm. 2004 47: 359; Wiltshire H R, J. Label. Cmpd. Radiopharm. 2001 44: 149; Lambert J B et al., J. Am. Chem. Soc. 1967: 5921.

Scheme IV

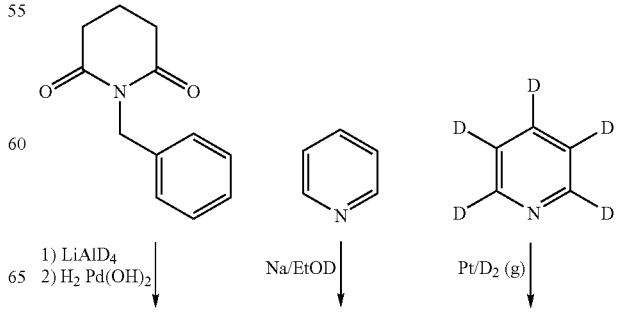

1) LiAlD$_4$
2) H$_2$ Pd(OH)$_2$

Na/EtOD

Pt/D$_2$ (g)

-continued

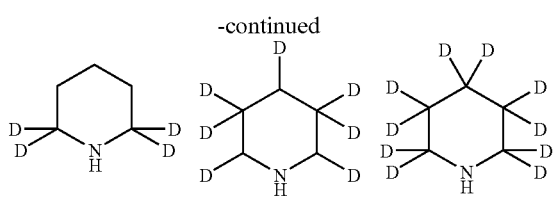

As shown in Scheme IV, the 2,2,6,6,-tetradeuteropiperidine precursor to the preferred compounds of Formula II wherein $Y^{1a}, Y^{1b}, Y^{2a}$, and $Y^{2b}$ are deuterium may be obtained by reduction of 2,6-dioxopiperidine or its N-protected analogs, for instance N-benzyl or N-4-methoxyphenyl, with agents such as $LiAlD_4$ or DIBAL-d (e.g. see Kalvin D M and Woodward R D, Tetrahedron 1984 40: 3387). Removal of the protecting group by means known in the art provides the deuterated piperidine, which then may be converted to the corresponding hydrazine and incorporated into the compound of Formula II. 2,3,3,4,5,5,6-Heptadeuteropiperidine, precursor to compounds of Formula II wherein all piperidine Y and Z groups except $Y^{1a}, Z^{2a}$ and $Y^{2a}$ are deuterium, can be conveniently obtained by dissolving metal reduction of pyridine in ethanol-d ($CH_3CH_2OD$) with sodium metal, under which conditions exchange of hydrogen for solvent deuterium occurs at the 3 and 5-positions; see Vierhapper F W et al., J. Org. Chem. 1975 40: 2734. If the readily available 2,6-dibromopyridine is subjected to halogen-deuterium exchange, for instance by metallation and deuterium oxide quench, or by catalytic reduction with deuterium gas (e.g. see Yadav J S et al., Adv. Synth. Catal. 2004 346: 77; and Kirefu T, et al. J. Label. Compd. Radiopharm. 2001 44: 329), the resulting 2,6-dideuteriopyridine may be subjected to sodium/ethanol-d reduction as above to yield the 2,2,3,3,4,5,5,6,6,-nonadeuteropiperidine precursor to the preferred compounds of Formula II wherein all piperidine Y and Z groups except $Z^{2b}$ are deuterium (not shown). The 2,2,3,3,4,4,5,5,6,6-decadeuteropiperidine precursor to the more preferred compounds of Formula II wherein all piperidine Y and Z groups are deuterium can be obtained by analogous reducing metal reduction, or for instance by catalytic reduction under deuterium gas, starting from the readily commercially available pentadeuteropyridine (e.g. from Aldrich Chemicals, Cambridge Isotope Laboratories, C/D/N Isotopes). Piperidine-$d_{11}$, in which each hydrogen in the piperidine ring has been replaced with deuterium, is also an item of commerce.

Introduction of fluorine into piperidine derivatives of formula VII can be carried out in a variety of ways. For instance, fluorination of oxopiperidines and thioketone-substituted piperidines, N-protected as necessary, can be carried out using aminosulfur trifluoride derivatives (e.g. see Singh R P and Shreeve J, Synthesis 2002 17: 2561; Mase T et al., J. Org. Chem. 2001 66: 6775). Electrophilic fluorination α to ketone groups is well known in the art and can be accomplished with agents such as N-fluoro amines and N-fluoro sulfonamides; see e.g. Sudlow K and Woolf A A, J. Fluorine Chem. 1994 66: 9; Wilkinson J A, Chem. Rev. 1992 92: 505; Singh R P and Shreeve J, Acc. Chem. Res. 2004 37: 31; Stavber G et al., Org. Lett. 2004 6: 4973. Numerous fluorinated reagents are available that can be converted into piperidine rings by means known in the art.

These fluorine and deuterium-substituted 1-aminopiperidines can also be incorporated into compounds of Formula IIA using known or readily prepared starting materials as illustrated in Scheme V. In this scheme, $R^{10}$ represents methyl or a halide, particularly bromine. Compounds of formula IX are prepared according to known methods; Barth F et al., US Patent Application 20040039024, Sanofi-Synthelabo Applicant. Reaction of the 4-bromomethyl substituent or equivalent leaving group with a deuterium-substituted methyl cuprate reagent is carried out by means described by Corey E J and Posner G H, J. Am. Chem. Soc. 1968 90: 5615. Variations in reactants and reaction conditions will be evident to those of ordinary skill in organic synthesis and process chemistry development and can be confirmed through routine experimentation.

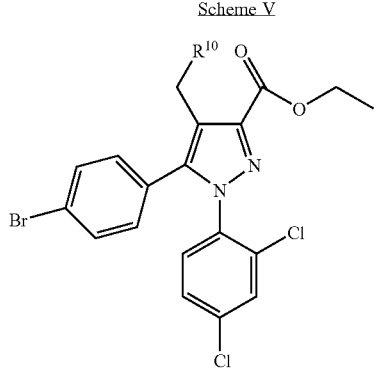

Formula IX $R^{10}$ = Br    $R^{10}$ = $CH_3$

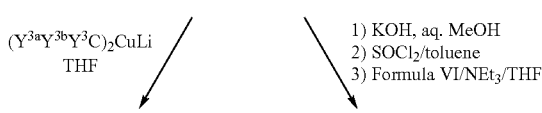

-continued

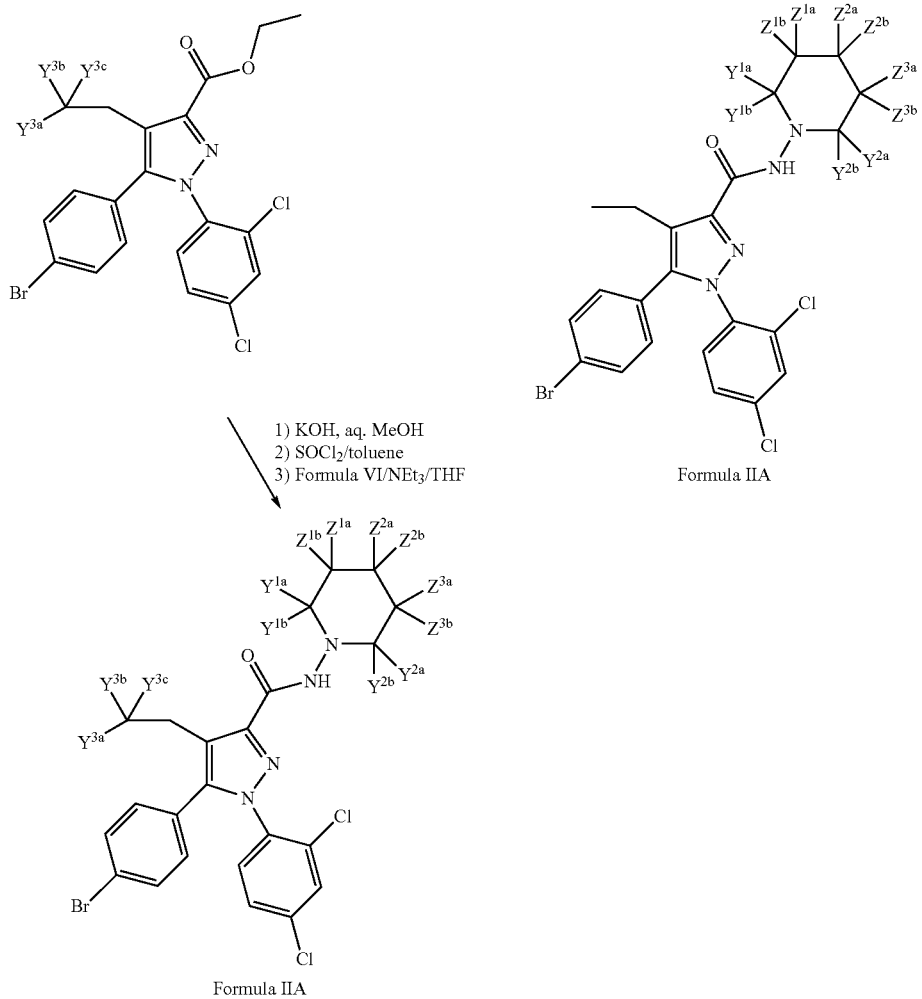

Formula IIA $^{13}$C-containing isotopologues of this invention can be prepared according to synthetic approaches referenced herein, or by preparation of starting materials for those syntheses, using readily available $^{13}$C-labeled starting materials. Suitable commercial supplies of such $^{13}$C-labeled reagents include, among others, Isotec, Inc. (Miamisburg, Ohio); Cambridge Isotope Laboratories (Andover, Mass.); ICON Services Inc. (Summit, N.J.); and C/D/N Isotopes, Inc. (Pointe-Claire, Quebec, Canada).

Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, $2^{nd}$ Edition, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artisan by use of commercially available structure-searchable database software, for instance, SciFinder (CAS division of the American Chemical Society) and CrossFire Beilstein (Elsevier MDL), or internet search engines such as Google® or keyword databases such as the US Patent and Trademark Office text database.

The synthetic methods described herein may additionally include steps, either before or after any of the steps described in Scheme II, to add or remove suitable protecting groups in order to ultimately allow synthesis of a particular compound of Formula II.

According to another embodiment, the invention provides any of above-described intermediate compounds of Formula IV or V, with each hydrogen and carbon atom contained therein optionally substituted by deuterium and $^{13}$C, respectively, with the restriction that if two or more Z atoms are not fluorine, then at least one hydrogen is replaced by deuterium, or at least one $^{12}$C atom is replaced by $^{13}$C.

The compounds of the present invention may contain one or more asymmetric carbon atoms. As such, a compound of this invention can exist as the individual stereoisomers (enantiomers or diastereomers) as well a mixture of stereoisomers. Accordingly, a compound of the present invention will include not only a stereoisomeric mixture, but also individual respective stereoisomers substantially free from one another stereoisomers. The term "substantially free of other stereoisomers" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing diastereomers are well known in the art and may be applied as practicable to final compounds or to starting material or intermediates. Other embodiments are those wherein the compound is an isolated compound.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to antagonism or inverse agonism of the $CB_1$ receptor).

The term "isotopologue" refers to species that differ from a specific compound of this invention only in the isotopic composition of their molecules or ions. The terms "lighter isotopologue" and "lighter atom isotopologue" as used herein, refer to species that differs from a specific compound of this invention in that they comprise one or more light isotopic atoms ($^1H$ or $^{12}C$) at positions occupied by a deuterium or $^{13}C$ in that specific compound. For the purposes of this invention, $^{11}C$ is not referred to as a light isotope of carbon.

A specific compound of this invention may also be referred to as a "heavy atom isotopic compound" to distinguish it from its lighter isotopologues when discussing mixtures of isotopologues.

Chemical naming terminology can be complex and different chemical names can often reasonably be applied to the same structure. To avoid any confusion, "Compound 1" refers to the free base chemical structure shown herein for that compound, wherein all hydrogen and carbon atoms are present at their natural isotopic abundance percentages. Similarly, "Compound 1A" refers to the free base chemical structure shown herein for that compound, wherein all hydrogen and carbon atoms are present at their natural isotopic abundance percentages.

It will be recognized that some variation of natural isotopic abundance occurs in a synthesized compound depending upon the origin of chemical materials used in the synthesis. Thus, a preparation of Compound 1 will inherently contain small amounts of deuterated and/or $^{13}C$-containing isotopologues. The concentration of naturally abundant stable hydrogen and carbon isotopes, notwithstanding this variation, is small and immaterial with respect to the degree of stable isotopic substitution of compounds of this invention. See for instance Wada E and Hanba Y, Seikagaku 1994 66: 15; Ganes L Z et. al., Comp. Biochem. Physiol. A Mol. Integr. Physiol. 1998 119: 725. The compounds of the present invention are distinguished from such naturally occurring minor forms in that the term "compound" as used in this invention refers to a composition of matter that is predominantly a specific isotopologue.

A "compound", as defined herein, contains less than 10%, preferably less than 6%, and more preferably less than 3% of all other isotopologues combined, including a form that lacks any deuterium or $^{13}C$. Compositions of matter that contain greater than 10% of all other isotopologues combined are referred to herein as "mixtures" and must meet the parameters set forth below. These limits of isotopic composition and all references to isotopic composition herein, refer solely to the relative amounts of deuterium/hydrogen and $^{13}C/^{12}C$ present in the active, free base form of the compound of Formula I, and do not include the isotopic composition of hydrolyzable portions of prodrugs, or of counterions.

The term "heavy atom" refers to isotopes of higher atomic weight than the predominant naturally occurring isotope.

The term "stable heavy atom" refers to non-radioactive heavy atoms.

Both "$^2H$" and "D" refer to deuterium.

"Stereoisomer" refers to both enantiomers and diastereomers

"cAMP" refers to cyclic adenosine monophosphate

"Antagonist" refers to both antagonists and inverse agonists

"MeOH" refers to methanol

"EtOH" refers to ethanol

"Et" refers to ethyl

"THF" refers to tetrahydrofuran

"DMF" refers to N,N-dimethylformamide

"aq." refers to aqueous

"h" refers to hours

"min" refers to minutes

"brine" refers to saturated aqueous sodium chloride

"US" refers to the United States of America

"FDA" refers to Food and Drug Administration

"NDA" refers to New Drug Application

"CAS" refers to the chemical abstracts service of the American Chemical Society

"5HT" refers to 5-hydroxytryptamine or serotonin

"PPAR" refers to peroxisome proliferator-activated receptor

The terms "ameliorate" and "treat" are used interchangeably and both mean decrease, suppress, attenuate, diminish, arrest, or stabilize the development or progression of a disease (e.g., a psychotic disorder).

By "disease" is meant any condition or disorder that damages or interferes with the normal function of a cell, tissue, or organ.

By "marker" is meant any protein or polynucleotide having an alteration in expression level or activity that is associated with a disease or disorder.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Both "patient" and "subject" used in the context of methods of treatment according to this invention refer to a mammal, preferably an economically important species such as pets and livestock, and more preferably a human.

The invention further provides compositions comprising a mixture of a compound of this invention and its lighter isotopologues. These mixtures may occur, for instance, simply as the result of an inefficiency of incorporating an isotope at a given position; intentional or inadvertent exchange of protons for deuterium, e.g. exchange of bulk solvent for heteroatom-attached deuterium; or intentional mixtures of pure compounds.

In one embodiment, such mixtures comprise at least about 50% of the heavy atom isotopic compound (i.e., less than about 50% of lighter isotopologues). More preferable is a mixture comprising at least 80% of the heavy atom isotopic compound. Most preferable is a mixture comprising 90% of the heavy atom isotopic compound.

In an alternate embodiment the mixture comprises a compound of Formula I and its lighter isotopologues in relative proportions such that at least about 50%, preferably at least 80%, more preferably at least 90%, even more preferably at least 95% and most preferably at least 98% of the compounds in said mixture comprise a stable heavy atom isotope at each position designated as a stable heavy atom isotope in the chemical formula of the heavy atom isotopic compound.

The following exemplifies this definition. A hypothetical compound of the invention contains deuterium at positions $Y^{1a}, Y^{2a}, Z^{1a}$ and $Z^{2a}$. A mixture comprising this compound and all of its potential lighter isotopologues and the relative proportion of each is set forth in the table below.

TABLE 1

|  | $Y^{1a}$ | $Y^{2a}$ | $Z^{1a}$ | $Z^{2a}$ | Relative Amt |
|---|---|---|---|---|---|
| Compound | D | D | D | D | 40% |
| Isotopologue 1 | D | D | H | D | 15% |
| Isotopologue 2 | D | D | D | H | 15% |
| Isotopologue 3 | H | D | D | D | 15% |
| Isotopologue 4 | D | H | H | D | 4% |
| Isotopologue 5 | H | D | H | D | 4% |
| Isotopologue 6 | H | H | D | H | 4% |
| Isotopologue 7 | H | D | H | H | 3% |
| % of compounds comprising an isotope at position $Y^{1a}$ | (40% + 15% + 15% + 4%) = 74% | 92% | 74% | 78% |  |

From the table it can be seen that the compound plus lighter isotopologues 1, 2 and 4 comprise the isotope deuterium at position $Y^{1a}$. These compounds are present in the mixture at relative amounts of 40%, 15%, 15% and 4%. Thus, 74% of the mixture comprises the isotope at $Y^{1a}$ that is present in the compound. The compound plus lighter isotopologues 1, 2, 3, 5 and 7 comprise the isotope deuterium at position $Y^{2a}$. These compounds are present in the mixture at relative amounts of 40%, 15%, 15%, 15%, 4% and 3%. Thus, 92% of the mixture comprises the isotope at $Y^{2a}$, that is present in the compound. The compound plus lighter isotopologues 2, 3 and 6 comprise the isotope deuterium at position $Z^{1a}$. These compounds are present in the mixture at relative amounts of 40%, 15%, 15% and 4%. Thus, 74% of the mixture comprises the isotope at $Z^{1a}$ that is present in the compound. The compound plus lighter isotopologues 1, 3, 4 and 5 comprise the isotope deuterium at position $Z^{2a}$. These compounds are present in the mixture at relative amounts of 40%, 15%, 15%, 4% and 4%. Thus, 78% of the mixture comprises the isotope at $Z^{2a}$ that is present in the compound. Accordingly, this mixture comprises a compound and its lighter isotopologues in relative proportions such that 74% of the compounds in said mixture comprise an isotope at each position containing a stable heavy atom isotope in the full isotopic compound.

The invention also provides compositions comprising an effective amount of a compound of Formula I (or any formulae herein), or a pharmaceutically acceptable prodrug, or prodrug salt thereof, or a solvate, hydrate, or polymorph, if applicable, of any of the foregoing; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued U.S. Patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein).

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. Surfactants such as sodium lauryl sulfate may be useful to enhance dissolution and absorption.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be administered in the form of suppositories for rectal or vaginal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to another embodiment, a compound of this invention may be incorporated into compositions for coating an implantable medical device, such as prostheses, artificial valves, vascular grafts, stents, or catheters. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings are optionally further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating or filling an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released form said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

The present invention further provides pharmaceutical compositions comprising an effective amount of one or more compound of the invention in combination with an effective amount of a second therapeutic agent useful for treating or preventing a condition selected from obesity, diabetes, and coronary artery disease.

Such second therapeutic agents useful in combination with the compounds of this invention include, but are not limited to: a norepinephrine transporter inhibitor, a ghrelin antagonist, a H3 antagonist/inverse agonist, a melanin-concentrating hormone 1 receptor antagonist, a melanin-concentrating hormone 2 receptor agonist/antagonist, a neuropeptide Y1 antagonist, a neuropeptide Y2 agonist, a neuropeptide Y4 agonist, a neuropeptide Y5 antagonist, a metabotropic glutamate subtype 5 receptor antagonist, leptin, a leptin agonist/modulator, a leptin derivative, an opioid antagonist, an orexin antagonist, a cholecystokinin-A agonist, ciliary neurotrophic factor (CNTF), a CNTF agonist/modulator, a CNTF derivative, a 5-hydroxytryptamine 2c agonist, a melanocortin 4 receptor agonist, a monoamine reuptake inhibitor, a serotonin reuptake inhibitor, a glucagon-like-peptide-1 agonist, topiramate, phytopharm compound 57, a COX-2 inhibitor, a PPARα agonist, an aldosterone antagonist, a lipase inhibitor; pharmaceutically acceptable salts, solvates, hydrates, and polymorphs of the foregoing; and combinations thereof.

Examples of norepinephrine transporter inhibitors include, but are not limited to, GW 320659, despiramine, talsupram, and nomifensine.

Examples of ghrelin antagonists include, but are not limited to, those disclosed in PCT Application Nos. WO 01/87335, and WO 02/08250. Ghrelin antagonists are also known as GHS (growth hormone secretagogue receptor) antagonists. The compositions and methods of the present invention therefore comprehend the use GHS antagonists in place of ghrelin antagonists.

Examples of H3 antagonist/inverse agonists include, but are not limited to, those disclosed in PCT Application No. WO 02/15905; and O-[3-(1H-imidazol-4-yl)propanol]carbamates (Kiec-Kononowicz K et al., Pharmazie 2000 55: 349-55 (2000)), piperidine-containing histamine H3-receptor antagonists (Lazewska D et al., Pharmazie 2001 56: 927), benzophenone derivatives and related compounds (Sasse A et al., Arch. Pharm.(Weinheim) 2001 334: 45), substituted N-phenylcarbamates (Reidemeister, S et al., Pharmazie 2000 55: 83), and proxifan derivatives (Sasse A et al., J. Med. Chem. 2000 43: 3335). Specific H3 antagonists/inverse agonists useful in the present invention include, but are not limited to, thioperamide, 3-(1H-imidazol-4-yl)propyl N-(4-pentenyl)carbamate, clobenpropit, iodophenpropit, imoproxifan, and GT2394 (Gliatech).

Examples of melanin-concentrating hormone 1 receptor antagonists and melanin-concentrating hormone 2 receptor agonist/antagonists include, but are not limited to, those disclosed in PCT Patent Application Nos. WO 01/82925, WO 01/87834, WO 02/06245, WO 02/04433, and WO 02/51809; and Japanese Patent Application No. JP 13226269. A specific melanin-concentrating hormone 1 receptor antagonist useful in the present invention includes, but is not limited to, T-226296 (Takeda).

Examples of neuropeptide Y1 antagonists include, but are not limited to, those disclosed in U.S. Pat. No. 6,001,836; and PCT Application Nos. WO 96/14307, WO 01/23387, WO 99/51600, WO 01/85690, WO 01/85098, WO 01/85173, and WO 01/89528. Specific examples of NPY1 antagonists useful in the present invention include, but are not limited to, BIBP3226, J-115814, BIBO 3304, LY-357897, CP-671906, and GI-264879A.

Examples of neuropeptide Y5 antagonists include, but are not limited to, those disclosed in U.S. Pat. Nos. 6,140,354; 6,191,160; 6,258,837; 6,313,298; 6,326,375; 6,335,345; 6,337,332, 6,329,395, and 6,340,683; European Patent Nos. EP-01010691, and EP-01044970; and PCT International Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/85714, WO 01/85730, WO 01/07409, WO 01/02379, WO 01/02379, WO 01/23388, WO,01/23389, WO 01/44201, WO 01/62737, WO 01/62738, WO 01/09120, WO 02/22592, WO 0248152, WO 02/49648, and WO 01/14376. Specific NPY 5 antagonists useful in the combinations of the present invention, include, but are not limited to 152,804, GW-569180A, GW-594884A, GW-587081X, GW-548118X; FR226928, FR 240662, FR252384; 1229U91, GI-264879A, CGP71683A, LY-377897, PD-160170, SR-120562A, SR-120819A and JCF-104. Additional specific NPY 5 antagonists useful in the combinations of the present invention, include, but are not limited to the compounds described in Norman et al., J. Med. Chem. 43: 4288-4312 (2000).

Examples of neuropeptide Y2 agonists include, but are not limited to, PYY3-36 as described in Batterham et al., Nature 2003 418: 650, NPY3-36, and other Y2 agonists such as N-acetyl [Leu(28,31)] NPY 24-36 (White-Smith and Potter, Neuropeptides 1999 33: 526), TASP-V (Malis et al., Br. J. Pharmacol. 1999 126: 989), cyclo-(28/32)-Ac-[Lys28-Glu32]-(25-36)-pNPY (Cabrele and Beck-Sickinger, J. Pept. Sci. 2000 6: 97).

Examples of thiazides include, but are not limited to, hydrochlorothiazide, flumethiazide, hydroflumethiazide, bendroflumethiazide, methylchlothiazide, trichlormethiazide, polythiazide or benzthiazide.

Examples of neuropeptide Y4 agonists include, but are not limited to, pancreatic peptide (PP) as described in Batterham et al., J. Clin. Endocrinol. Metab. 2003 88: 3989 and other Y4 agonists such as 1229U91 (Raposinho et al., Neuroendocrinology 2000 71: 2).

Examples of metabotropic glutamate subtype 5 receptor antagonists include, but are not limited to, 2-methyl-6-(phenylethynyl)-pyridine (MPEP) and (3-[(2-methyl-1,3-thiazol-4-yl)ethynyl]pyridine) (MTEP) and those compounds described in Anderson J et al., Eur. J. Pharmacol. 2003 473: 35; Cosford N et al., Bioorg. Med. Chem. Lett. 2003 13: 351; and Anderson J et al., J. Pharmacol. Exp. Ther. 2002 303: 1044.

Leptin includes, but is not limited to, recombinant human leptin (PEG-OB, Hoffinan La Roche) and recombinant methionyl human leptin (Amgen). Leptin derivatives (e.g., truncated forms of leptin) useful in the present invention include those disclosed in: U.S. Pat. Nos. 5,552,524; 5,552, 523; 5,552,522; 5,521,283; and PCT International Publication Nos. WO 96/23513; WO 96/23514; WO 96/23515; WO 96/23516; WO 96/23517; WO 96/23518; WO 96/23519; and WO 96/23520.

Examples of opioid antagonists include, but are not limited to, those disclosed by PCT Application No. WO 00/21509. Specific opioid antagonists useful in the present invention include, but are not limited to, nalmefene (Revex®), 3-methoxynaltrexone naloxone, and naltrexone.

Examples of orexin antagonists include, but are not limited to, those disclosed in PCT Patent Application Nos. WO 01/96302, WO 01/68609, WO 02/51232, and WO 02/51838. Specific orexin antagonists useful in the present invention include, but are not limited to, SB-334867-A.

Phytopharm compound 57 is also known as CP 644,673.

An example of an acyl-estrogen includes, but is not limited to, oleoyl-estrone (del Mar-Grasa M et al., Obes. Res. 2001 9:202.

Examples of cholecystokinin-A agonists include, but are not limited to, those disclosed in U.S. Pat. No. 5,739,106. Specific CCK-A agonists include, but are not limited to, AR-R 15849, GI 181771, JMV-180, A-71378, A-71623 and SR146131.

Examples of ciliary neurotrophic factors include, but are not limited to, GI-181771 (Glaxo-SmithKline); SR146131 (Sanofi Synthelabo); butabindide; PD170,292, PD 149164 (Pfizer). CNTF derivatives useful in the present invention include, but are not limited to, axokine (Regeneron); and those disclosed in PCT Application Nos. WO 94/09134, WO 98/22128, and WO 99/43813.

Examples of 5HT$_{2C}$ agonists include, but are not limited to, those disclosed in U.S. Pat. No. 3,914,250; and PCT Application Nos. WO 02/36596, WO 02/48124, WO 02/10169, WO 01/66548, WO 02/44152; WO 02/51844, WO 02/40456, and WO 02/40457. Specific 5HT2C agonists useful in this invention include, but are not limited to, BVT933, DPCA37215, WAY161503, and R-1065.

An example of a melanocortin receptor antagonist includes, but is not limited to, Melanotan-II (MT-II) as disclosed in U.S. Pat. No. 5,674,839. Melanocortin 4 receptor (Mc4r) agonists useful in the present invention include those disclosed in: PCT Application Nos. WO 01/991752, WO 01/74844, WO 02/12166, WO 02/11715, WO 02/12178, and US Patent Applications 20040092507 and 20050075344. Specific Mc4r agonists useful in the present invention include CHIR86036 (Chiron); ME-10142, and ME-10145 (Melacure).

Examples of monoamine reuptake inhibitors include, but are not limited to, those disclosed in PCT Application Nos. WO 01/27068, and WO 01/62341. Specific monoamine reuptake inhibitors useful in the present invention include, but are not limited to, sibutramine (Meridia®/Reductil®) disclosed in U.S. Pat. Nos. 4,746,680, 4,806,570, and 5,436,272, and U.S. Patent Publication Ser. No. 2002/0,006,964 and fenfluramine. The present invention encompasses sibutramine as a racemic mixture, as optically pure isomers (+) and (−), clathrate or prodrug thereof; particularly sibutramine hydrochloride monohydrate.

Examples of serotonin reuptake inhibitors include, but are not limited to, sertraline, fluvoxamine, paroxetine, fluoxetine, venlafaxine, mirtazapine, buspirone, trazodone, nefazadone, clomipramine, imipramine, nortriptyline, mianserine, duloxetine, dapoxetine, litoxetine, femoxetine, lofepramine, tomoxetine, citalopram, escitalopram, phentermine, dexfenfluramine, and those in disclosed in U.S. Pat. No. 6,365,633, and PCT published patent applications WO 01/27060 and WO 01/162341

Examples of glucagon-like-peptide-1 agonists include, but are not limited to, those disclosed in US Patent Application 20050153890.

Examples of COX-2 inhibitors include, but are not limited to, those disclosed in US Patent Application 20040204472. Specific monoamine reuptake inhibitors useful in the present invention include, but are not limited to, celecoxib, valdecoxib, deracoxib, rofecoxib, etoricoxib, JTE-522, or prodrugs thereof.

Examples of aldosterone inhibitors include, but are not limited to, those disclosed in US Patent Application 20040214804. Specific aldosterone inhibitors useful in the present invention include, but are not limited to: pregn-4-ene-7,21-dicarboxylic acid, 9,11-epoxy-17-hydroxy-3-oxo-γ-lactone, methyl ester, (7α,11α,17α)-; pregn-4-ene-7,21-dicarboxylic acid, 9,11-epoxy-17-hydroxy-3-oxo-dimethyl ester, (7α,11α,17α)-; 3'H-cyclopropa(6,7) pregna-4,6-diene-21-carboxylic acid, 9,11-epoxy-6,7-dihydro-17-hydroxy-3-oxo-γ-lactone, (6α,7α,11α,17α)-; pregn-4-ene-7,21-dicarboxylic acid, 9,11-epoxy-17-hydroxy-3-oxo-,7-(1-methylethyl) ester, mono potassium salt,(7α,11α,17α)-; pregn-4-ene-7,21-dicarboxylic acid, 9,11,-epoxy-17-hydroxy-3-oxo-,7-methyl ester, mono potassium salt, (7α,11α, 17α)-; 3'H-cyclopropa(6,7)pregna-1,4,6-triene-2-1-carboxylic acid, 9,11-epoxy-6,7-dihydro-17-hydroxy-3-oxo-γ-lactone-(6α,7α, 11α)-; 3'H-cyclopropa(6,7)pregna-4,6-diene-21-carboxylic acid, 9,11-epoxy-6,7-dihydro-17-hydroxy-3-oxo-, methyl ester, (7α, 11α,17α)-; 3'H-cyclopropa(6,7)pregna-4,6-diene-21-carboxylic acid, 9,11-epoxy-6,7-dihydro-17-hydroxy-3-oxo-, mono potassium salt, (6α,7α,11α,17α)-; 3'H-cyclopropa(6,7)pregna-4,6-diene-21-carboxylic acid, 9,11-epoxy-6,7-dihydro-17-hydroxy-3-oxo-, γ-lactone, (6α,7α,11α, 17α)-; pregn-4-ene-7,21-dicarboxylic acid, 9,11-epoxy-17-hydroxy-3-oxo-,γ-lactone, ethyl ester, (6α,7α,11α,17α)-; and pregn-4-ene-7,21-dicarboxylic acid, 9,11-epoxy-17-hydroxy-3-oxo-, γ-lactone, 1-methylethyl ester, (7α,11α,17α)-.

Examples of lipase inhibitors include, but are not limited to, orlistat, panclicins, ATL-962, and lipstatin.

In another embodiment, the invention provides separate dosage forms of a compound of this invention and a second therapeutic agent, wherein said compound and said second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, a compound of the present invention is present in an effective amount. As used herein, the term "effective amount" refers to an amount which, when administered in a proper dosing regimen, is sufficient to reduce or ameliorate the severity, duration or progression, or enhance function compromised by a disorder responsive to antagonism or inverse agonism of the $CB_1$ receptor; to cause the regression of a disorder associated with signal transduction by the $CB_1$ receptor; or to enhance or improve the prophylactic or therapeutic effect(s) of another therapy.

In certain preferred embodiments, treatment according to the invention provides a reduction in or prevention of at least one symptom or manifestation of a disorder that has been linked to activity at the $CB_1$ receptor, as determined by in vivo or in vitro antagonism or reverse agonism of at least about 10%, more preferably 20%, 30%, 40%, 50%, 60%, 70%, 80%, 90%, 95%, 98% or 99% of such activity. With respect to antagonism or reverse agonism of the $CB_1$ receptor the term "effective amount" means an amount that results in one or more of: reversal of forskolin-induced accumulation of cAMP in cells stably expressing $CB_1$ receptors that are stimulated by a known CB agonist (e.g. (R)-WIN-55212-2 or CP-55,940); inhibition of $[^{35}S]GTP\gamma S$ binding in cells expressing $CB_1$ receptors that are stimulated by a known CB agonist (e.g. anandamide); the correction of or relief from a behavior, deficit, symptom, syndrome or disease, or enhancement of otherwise compromised function that has been linked $CB_1$ receptor activity or that is known to be responsive to antagonism or inverse agonism of the $CB_1$ receptor, alone or in combination with another agent or agents; or the induction of a behavior, activity or response that has been linked to antagonism or inverse agonism of $CB_1$ receptors.

The interrelationship of dosages for animals and humans (based on milligrams per meter squared of body surface) is described in Freireich et al., (1966) Cancer Chemother. Rep. 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, yet more preferably 0.025 mg/kg to about 1.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise second therapeutic agents, an effective amount of the other agent is between about 20% and 100% of the dosage normally utilized in a monotherapy regime using just that additional agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents listed above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In one embodiment, the invention provides a method of inhibiting the $CB_1$ receptor, in a biological sample comprising the step of contacting said biological sample with a compound of Formula I. The term "biological sample," as used herein, refers to a fluid, an organ, a tissue, or a cell derived from an animal, as well as a transformed or otherwise manipulated cell in culture or transplanted into an animal.

In one embodiment, the present invention provides a method of causing antagonism or inverse agonism of the $CB_1$ receptor in a subject, comprising the step of administering to said subject an effective amount of a compound of this invention, preferably as part of a composition additionally comprising a pharmaceutically acceptable carrier. Preferably, this method is employed to treat a subject suffering from or susceptible to one or more disease or disorder selected from obesity, poorly regulated consumption desires, disorders associated with a substance, obesity associated with non-insulin-dependent diabetes, treating obesity associated with dyslipidemia, diseases resulting in patients becoming overweight, bulimia, drug dependency, the desire to consume non-essential food items and the spontaneous appetency for a food item which usually brings pleasure, and neuroinflammatory pathology, particularly that involving demyelinization, viral encephalitis, cerebrovascular accidents, or cranial trauma.

In another embodiment, the invention provides a method of treating a subject suffering from or susceptible to one or more disease or disorder selected from diarrhea; obesity in juvenile patients, including in cases of drug-induced obesity; dyslipidemia and dislipidemia-associated diseases such as metabolic syndrome, Parkinson's disease; hepatic diseases including liver fibrosis, alcoholic cirrhosis, chronic viral hepatitis non-alcoholic steatohepatitis, and primary liver cancer; Parkinson's disease; itch; sexual dysfunction; and bone disorders, comprising the step of administering to said subject an effective amount of a compound of this invention, preferably as part of a composition additionally comprising a pharmaceutically acceptable carrier. Other embodiments include any of the methods herein wherein the subject is identified as in need of the indicated treatment.

More preferably, the condition to be treated is selected from obesity, smoking, obesity associated with dyslipidemia, obesity associated with non-insulin-dependent diabetes, alcohol abuse, and normalization of blood lipid composition.

In another embodiment, the method of treatment further comprises the step of administering to said patient a second therapeutic agent that is effective to treat diabetes or obesity.

In still another embodiment, the method of treatment additionally comprises the administration of a second therapeutic to reduce smoking. Such therapeutics include a nicotine patch and nicotine gum.

In yet another embodiment, the method of treatment comprises the further step of administering to said patient a second therapeutic agent that is effective to treat one or more of obesity effects and coronary artery disease.

In each of the above embodiments, the second therapeutic agent may be administered together with a compound of this invention as part of a single dosage form or as separate dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administering of the second therapeutic agent may occur before, concurrently with, and/or after the administering of the compound of this invention. When administration of the second therapeutic agent occurs concurrently with a compound of this invention, the two (or more) agents may be administered in a single dosage form (such as a composition of this invention comprising a compound of the invention and an second therapeutic agent as described above), or in separate dosage forms. The administration of a composition of this invention comprising both a compound of the invention and a second therapeutic agent to a subject does not preclude the separate administration of said second therapeutic agent, any other therapeutic agent or any compound of this invention to said subject at another time during a course of treatment.

Effective amounts of a second therapeutic agent useful in the methods of this invention are well known to those skilled in the art and guidance for dosing may be found in patents referenced herein. However, it is well within the skilled artisan's purview to determine the second therapeutic agent's optimal effective-amount range. In one embodiment of the invention where a second therapeutic agent is administered to an animal, the effective amount of the compound of this invention is less than its effective amount would be where the second therapeutic agent is not administered. In another embodiment, the effective amount of the second therapeutic agent is less than its effective amount would be where the compound of this invention is not administered (i.e., the amount of second therapeutic agent administered in a monotherapy). In this way, undesired side effects associated with high doses of either agent may be minimized. Other potential advantages (including without limitation improved dosing regimens and/or reduced drug cost) will be apparent to those of skill in the art.

Second therapeutic agents useful in the methods of treatment of this invention are the same as those described above as part of combination compositions.

The compounds of this invention may be assayed for activity in vitro by known methods. For instance, recombinant human $CB_1$ signal transduction assays ($[^{35}S]$-GTPγS binding) are available at MDS Pharma Services, as are $CB_2$ binding counterscreens. Methodology for such assays is also well known; see for instance Devane W A et al, Science 1992 258: 1946; Rinaldi-Carmona M et al. FEBS Lett. 1994 350: 240; and Gonsiorek W et al., Mol. Pharmacol. 2000 57: 1045. The compounds may also be assayed by measuring reversal of forskolin-induced accumulation of cAMP in cells stably expressing $CB_1$ receptors that are stimulated by a known CB agonist (e.g. (R)-WIN-55212-2 or CP-55,940); for instance, see Matsuda L A et al., Nature 1990 346: 561; and Rinaldi-Carmona M et al., J. Pharmacol. Exp. Ther. 1996 278: 871.

Animal models measuring weight reduction in obese animals, reduction of ethanol intake, and reversal of known cannabinoid agonist's activity, are also available and provide in vivo measurements of the central $CB_1$ receptor antagonist activity of compounds of this invention, as well as their duration of action. See e.g. Rinaldi-Carmona M et al. FEBS Lett. 1994 350: 240; Arnone M et al., Psychopharmacology 1997 132: 104; and Trillou C R et al., Am. J. Physiol. Regul. Integr. Comp. Physiol. 2003 284: R345; Campbell U C and Carroll M E, Exp. Clin. Psychopharmacol. 2000 8: 312. Each of the compounds of this invention may be tested by such means.

The compounds of the invention may also be tested by in vitro assays, for resistance to liver metabolism by cellular or tissue exposure, by exposure to isolated metabolic enzymes such as recombinant cytochrome P450s, or by in vivo pharmacokinetic measurement (available commercially, e.g. from SRI Biosciences, Menlo Park, Calif.; Covance, Princeton N.J.; Charles River Laboratories, Wilmington, Mass.; and Cerep, Seattle Wash.; among others) and compared to Compound 1 or Compound 1A.

Diagnostic Methods and Kits

According to another embodiment, the invention provides a method of determining the concentration of a first compound selected from Compound 1 or Compound 1A in a biological sample, said method comprising the steps of:

a) adding a known concentration of a second compound to said biological sample, said second compound having, for the determination of Compound 1 the formula:

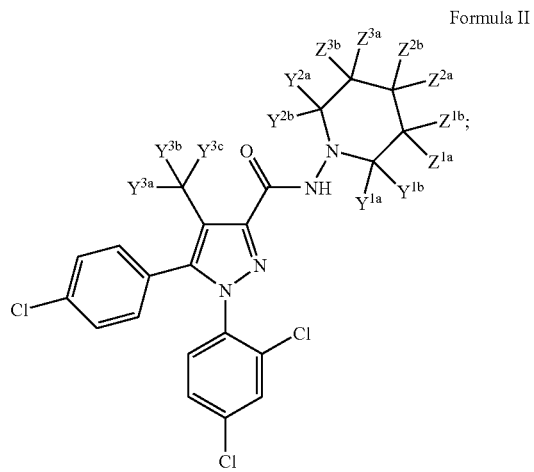

Formula II and for the determination of Compound IA, the formulae:

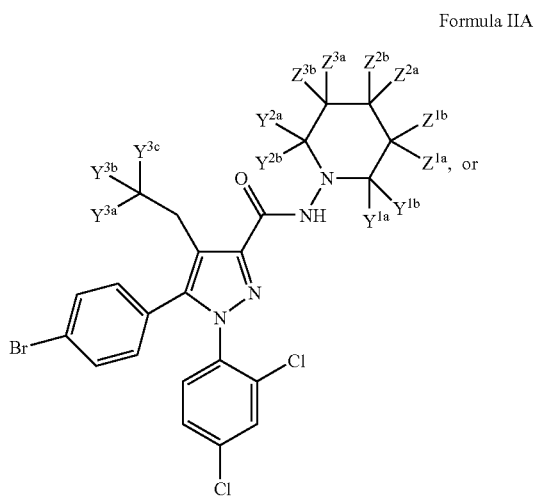

Formula IIA

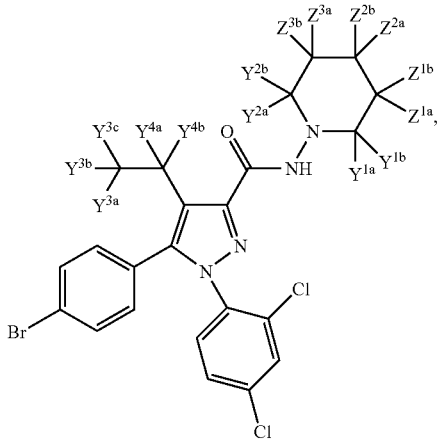

Formula IIB or a salt thereof, or a hydrate, solvate and/or polymorph of said compound or salt;

wherein:
each Y is independently deuterium or hydrogen;
each Z is independently deuterium or hydrogen;
at least one Y or at least one Z is deuterium;
each independent hydrogen other than Y or Z is optionally replaced with deuterium;
each independent carbon is optionally replaced with $^{13}C$; and
the compound contains at least 4 total deuterium and $^{13}C$ atoms (i.e. (total number of D)+(number of $^{13}C$)$\geq$4)

b) subjecting said biological sample to a measuring device that distinguishes the first compound from said second compound;

c) calibrating said measuring device to correlate the detected quantity of the first compound with the known concentration of said second compound added to said biological sample; and d) determining the concentration of said first compound in said biological sample by comparing the detected quantity of said first compound with the detected quantity and known concentration of said second compound.

Measuring devices that can distinguish the first compound from said second compound include any measuring device that can distinguish between two compounds that are of identical structure except that one contains one or more heavy atom isotope versus the other. Preferably, such a measuring device is a mass spectrometer.

In a preferred embodiment, at least seven combined hydrogen atoms and carbons are, respectively, replaced by deuterium and $^{13}C$ in said second compound; i.e. (total number of D)+(number of $^{13}C$)$\geq$7.

In another preferred embodiment, the method comprises the additional step of organically extracting both the first compound and said second compound from said biological sample prior to step b).

The first compound and the corresponding second compound will have similar solubility, extraction, and chromatographic properties, but significantly different molecular mass. Thus, the second compound is useful as an internal standard in a method that comprises the step of organic extraction to measure the efficiency of that extraction and to ensure an accurate determination of the true concentration of Compound 1 (see Tuchman M and McCann M T, Clin. Chem. 1999 45: 571; Leis H J et al., J. Mass Spectrom. 2001 36: 923; Taylor R L et al. Clin. Chem. 2002 48: 1511).

The compounds of the present invention (the second compound) are particularly useful in this method since they are not radioactive and therefore do not pose a hazard to personnel handling the compounds. Thus, these methods do not require precautions beyond those normally applied in clinical sample analysis.

In another embodiment, the invention provides a diagnostic kit comprising:

a) a compound having the Formula II:

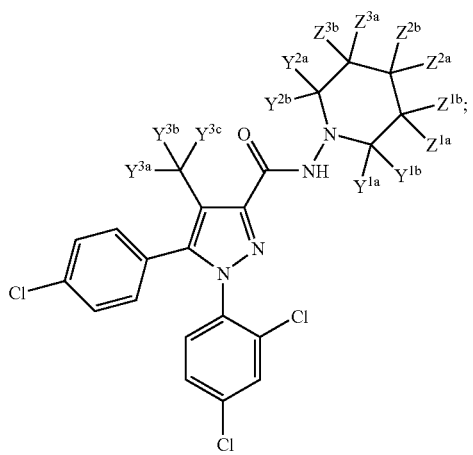

Formula IIA:

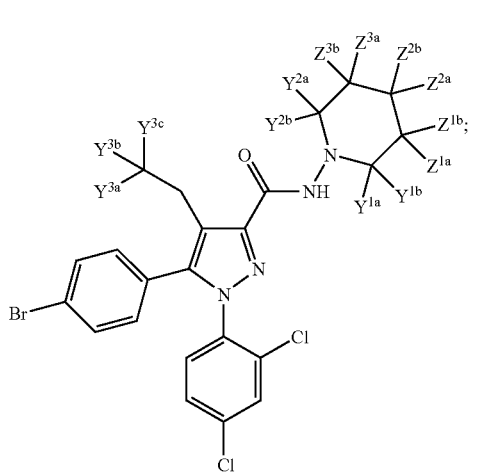

or Formula IIB

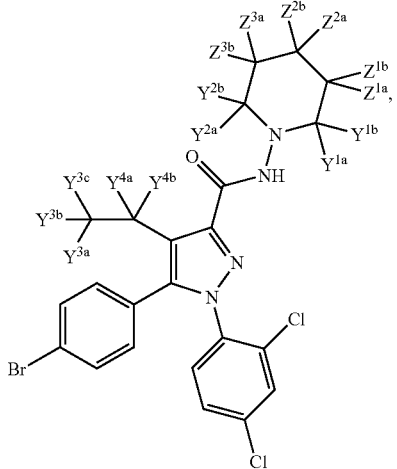

a salt thereof; or a hydrate or a solvate or a polymorph thereof; wherein:

each Y is independently deuterium or hydrogen;
each Z is independently deuterium or hydrogen;
at least one Y or at least one Z is deuterium;
each independent hydrogen other than Y or Z is optionally replaced with deuterium;
each independent carbon is optionally replaced with $^{13}C$; and
the compound contains at least 4 total deuterium and $^{13}C$ atoms (i.e. (total number of D)+(number of $^{13}C$)$\geq$4); and b) instructions for using said compound to determine the concentration of a test compound in a biological sample.

Stably labeled isotopes have long been used to assist in research into the enzymatic mechanism of cytochrome P450 enzymes (Korzekwa K R et al., Drug Metab. Rev. 1995 27: 45 and references therein; Kraus, J A and Guengerich, F P, J. Biol. Chem. 2005 280: 19496; Mitchell K H et al., Proc. Natl. Acad. Sci. USA 2003 109: 3784).

In another embodiment, the invention provides a method of evaluating the metabolic stability of a compound of this invention, particularly a compound of Formula II, IIA or IIB, comprising the steps of contacting the compound with a metabolizing enzyme source for a period of time; and comparing the amount of said compound and metabolic products of said compounds after said period of time.

In one preferred embodiment, the method comprises an additional step of comparing the amount of said compound and said metabolic products of said compounds at an interval during said period of time. This method allows the determination of a rate of metabolism of said compound.

In another preferred embodiment, the method of evaluating the metabolic stability of a compound of this invention comprises the additional steps of: contacting the compound with said metabolizing enzyme source; comparing the amount of compound and its respective metabolic products after said period of time to determine its metabolic stability; and comparing the metabolic stability with the metabolic stability of the corresponding non-isotopic compound. Preferably, the non-isotopic compound utilized in such method is Compound 1 or Compound 1A and, the compound of the invention used in such method is a compound of Formula II, IIA, or IIB. This method is useful in determining whether and at which sites on a compound of this invention additional deuterium or $^{13}C$ substitution would cause increases in metabolic stability. It is also particularly useful in comparing the metabolic stability of a compound, respectively, of Formula II; or IIA or IIB, with the metabolic stability of Compound 1 or 1A.

A metabolizing enzyme source may be a purified, isolated or partially purified metabolic protein, such as a cytochrome P450; a biological fraction, such as a liver microsome fraction; or a piece of a metabolizing organ, such as a liver slice.

The determination of the amount of compound and its metabolic products is well known in the art. It is typically achieved by removing an aliquot from the reaction mixture and subjecting it to an analysis capable of distinguishing between the compound and its metabolites, such as reversed-phase HPLC with UV absorption or mass spectroscopic detection. Concentrations of both the metabolizing enzyme and the compound may be varied to determine kinetic parameters, for instance, by using appropriate nonlinear regression software such as is known in the art. By comparing the kinetic parameters of both a compound of this invention and its non-isotopic counterpart, an apparent steady-state deuterium isotope effect ($^D(V/K)$) can be determined as the ratio of products formed in the hydrogen versus deuterium reactions.

The determination of a rate of metabolism of a compound of this invention, particularly a compound of Formula II, IIA or IIB may be achieved in a reaction separate from the reaction for determining the metabolism rate of Compound 1 or Compound 1A. Alternatively, Compound 1 or Compound 1A may be admixed, respectively, with the corresponding compound of Formula II, IIA or IIB in a competition experiment to determine rates of disappearance of the two compounds, making use of analytical instrumentation capable of differentiating between the two compounds based on their mass differences.

In yet another embodiment, pre-steady state kinetics, such as $V_0$, may be determined by means known in the art, for instance, using quench-flow apparatus, by monitoring the quenched reactions at varying times after mixing the compound or isotopologue with the metabolizing enzyme source.

In a related embodiment, the invention provides a kit comprising, in separate vessels: a) a compound of any of the formulae herein; and b) a metabolizing enzyme source. Preferably, the compound is a compound of Formula II, IIA or IIB. The kit is particularly useful for comparing the metabolic stability of a compound of Formula II, IIA or IIB with the corresponding Compound 1 or Compound 1A, as well as evaluating the effect of deuterium and $^{13}C$ replacement at various positions on a compound of Formula II, IIA or IIB. In a preferred embodiment, the kit further comprises instructions for using a compound of Formula II, IIA or IIB and said metabolizing enzyme source to evaluate the metabolic stability of said compound of Formula II, IIA or IIB.

In order that the invention might be more fully understood, the following examples are set forth. They are not intended to limit the scope of the invention and further examples will be evident to those of ordinary skill in the art. In each example set forth herein, carbon shall be $^{12}C$, and hydrogen shall by $^1H$, each incorporated at its natural abundance, unless otherwise specified. All solvents used in the Examples are anhydrous unless otherwise specified.

Example 1: 1-Benzyl-2,2,6,6-tetradeuteropiperidine. Dissolve 12.4 mmol of 1-benzylpiperidine-2,6-dione (e.g. see Tateoka Y et. al. Res. Commun. Chem. Pathol. Pharmacol. 1988 61: 315) in 20 mL of THF. Add this solution dropwise under argon to a cold (ice bath) suspension of 24.8 mmol of $LiAlD_4$ in 50 mL of THF during 20 min. Remove ice bath, stir for 16 h at room temperature. Decompose excess $LiAlD_4$ by careful dropwise addition of 0.47 mL water, 0.47 mL of 15% aq. NaOH, and 1.4 mL of water. Filter the resulting suspension through Celite® and concentrate in vacuo. Purify by silica gel column chromatography using concentrated $NH_4OH$/methanol/methylene chloride eluant to yield the title compound.

Example 2: 2,2,6,6-Tetradeuteropiperidine. Dissolve 7.7 mmol of the product of Example 1 in 15 mL of methanol under argon. Add 140 mg of $Pd(OH)_2/C$ (20% loading on carbon, wet with 50% water content). Stir under 20 psig of hydrogen for 6 h. Filter through Celite®, washing with additional methanol. Distill off methanol using a short fractionation column to leave ca. 4 mL of residue. Distill this residue in a Kugelrohr apparatus to yield the title compound.

Example 3: 2,2,6,6-Tetradeuteropiperidin-1-amine hydrochloride. Dissolve 4.8 mmol of the product of Example 2 in 12 mL of acetic acid and 3 mL of water. Cool in an ice/water bath and add 5.8 mmol of sodium nitrite in portions during 30 min. Stir for an additional hour, then add 19.2 mmol of zinc dust in portions. Stir for 1 h, filter, and concentrate the filtrate in vacuo. Partition the residue between saturated sodium bicarbonate and methylene chloride. Extract the organic layer with additional methylene chloride. Dry the combined organic phases over $MgSO_4$ and concentrate in vacuo. Dissolve the residue in 10 mL of dry ether and treat under argon with 1.2 mL of anhydrous HCl in dioxane, cool in an ice bath under nitrogen for 1 h. Filter and wash with additional ether to yield the title compound.

Example 4: 2,2,3,3,4,4,5,5,6,6-Decadeutero-1-nitrosopiperidine. Dissolve a 29.1 mmol portion of piperidine-$d_{11}$ in 80 mL of 1N HCl and cool in an ice/salt bath. While stirring, add a solution of 35 mmol of sodium nitrite in 30 mL of water during about 40 min. Stir for 1 h after completion of addition, then adjust pH to about 10-11 by addition of 2N NaOH. Extract with ethyl acetate three times, combine organic phases, and wash with brine. Dry over $MgSO_4$ and concentrate to yield the title compound as a crude oil, which is used without further purification.

Example 5: 2,2,3,3,4,4,5,5,6,6-Decadeuteropiperidin-1-amine hydrochloride. Dissolve the entire product of Example 4, less a small retained analytical sample, in 20 mL of THF. Add dropwise during 30 min under argon to a stirred suspension of 28 mmol of $LiAlH_4$ in 80 mL of THF. Heat under reflux for 1 h, remove the heating bath and stir an additional 3 h at room temperature. Cool in an ice/water bath and cautiously decompose excess $LiAlH_4$ by addition of 1.06 mL of water, 1.06 mL of 15% NaOH, and 3.18 mL of water. Filter through celite, wash with additional THF. Concentrate the filtrate in vacuo. Dissolve the filtrate in 40 mL of dry ether, cool in an ice/water bath under argon and treat with ca. 7 mL of 4.2 N HCL in dioxane. After standing for 2 h, filter, washing the filtrate with additional ether, to yield the title compound.

Example 6: Diethyl 2,2,4,4,-tetrafluoro-3-oxopentanedioate hydrate. Treat a 17.5 mmol sample of diethyl 3-oxopentanedioate with 90 mL of aqueous 0.5% sodium laureth sulfate (Genapol LRO) and stir for 12 min at 60° C. Add 73.5 mmol of 1-chloromethyl-4-fluoro-1,4-diazoniabicyclo[2.2.2]octane bis(tetrafluoroborate) and stir vigorously for 4.5 h. Cool the reaction to room temperature and extract twice with methylene chloride. Combine organic extracts and wash with half-saturated brine. Dry over $MgSO_4$, concentrate in vacuo and purify the residue by silica gel chromatography using ethyl acetate/hexanes eluant to yield the title compound.

Example 7: Diethyl 2,2,3,3,4,4,-hexafluoropentanedioate. Dissolve 6.7 mmol of the product of Example 6 is 25 mL of methylene chloride and add 11.4 mmol of bis(2-methoxyethyl)aminosulfur trifluoride. Heat under reflux for 15 h. Cool to room temperature and partition between 50 mL each of ether and saturated sodium bicarbonate. Wash organic layer with 1 N HCl and brine, dry over $MgSO_4$, concentrate in vacuo and purify the residue by silica gel chromatography using ethyl acetate/hexanes eluant to yield the title compound.

Example 8: 1-Benzyl-3,3,4,4,5,5-hexafluoropiperidine-2,6-dione. Dissolve 3.4 mmol of benzylamine in 12 mL of methylene chloride and cool in an ice/water bath under argon. Add 4.1 mmol of trimethylaluminum as a 2 M hexane solution dropwise during several minutes. Stir for 10 min, then add 3.4 mmol of the product of Example 7 as a solution in 4 mL of methylene chloride. Remove ice bath and stir for 2 h at room temperature, then heat under reflux for 3 h. Cool in an ice/water bath and cautiously decompose excess trimethylaluminum with water. Partition the reaction mixture between 30 mL each of ether and water and wash the organic layer with 1N HCl, saturated sodium bicarbonate, and brine, then dry over $MgSO_4$ and concentrate in vacuo. Dissolve the residue in 2 mL of DMF and add to a slurry of 3.5 mmol of sodium hydride (washed with hexane twice to remove mineral oil) and 4 mL of DMF under argon. Stir for 16 h at room temperature. Cautiously decompose excess sodium hydride with several drops of water and partition the mixture between ethyl acetate and water. Extract the aqueous layer twice with more ethyl acetate, then wash the combined organic layers with 1N HCl, saturated sodium bicarbonate, and brine. Dry over $MgSO_4$ and concentrate in vacuo. Purify the residue by silica gel chromatography using ethyl acetate/hexanes eluant to yield the title compound.

Example 9: 1-Benzyl-3,3,4,4,5,5-hexafluoro-2,2,6,6,-tetradeuteropiperidine. Reduce 2.1 mmol of the product of Example 8 with lithium aluminum deuteride using the general procedure set forth in Example 1, and purify using silica gel chromatography using methylene chloride/methanol/saturated $NH_4OH$ as eluant to yield the title compound.

Example 10: 3,3,4,4,5,5-Hexafluoro-2,2,6,6,-tetradeuteropiperidine hydrochloride. Debenzylate 0.94 mmol of the product of Example 9 using the general procedure set forth in Example 2. Following removal of solvent, dissolve the residue in 5 mL of diisopropyl ether and cool in an ice/water bath under argon. Treat with a slow stream of gaseous HCl to form the salt. Remove the cold bath and blow off about half of the solvent under a stream of argon. Add about 8 mL of hexane and cool again at 0° C. for 17 h. Filter, washing with hexane, and dry in vacuo to yield the title compound.

Example 11: 3,3,4,4,5,5-Hexafluoro-2,2,6,6,-tetradeutero-1-nitrosopiperidine. Nitrosylate 0.72 mmol of the product of Example 10 using the general procedure set forth in Example 4 to yield the title compound, which is used directly in subsequent reactions.

Example 12: 3,3,4,4,5,5-Hexafluoro-2,2,6,6,-tetradeuteropiperidin-1-amine hydrochloride. Reduce the entire yield of the product of Example 11, except for a ca. 2 mg retained sample, according to the general procedure set forth in Example 5 to yield the title compound.

Example 13: Diethyl 3-thioxopentanedioate. Dissolve 14.1 mmol of diethyl 3-oxopentanedioate in 15 mL of toluene under argon add 49.4 mmol of sodium bicarbonate and 15.1 mmol of Lawesson's reagent. Stir for 1 h at room temperature then heat under reflux for 5 h. Cool, filter, and concentrate in vacuo. Purify the residue by silica gel chromatography using ethyl acetate/hexanes eluant to yield the title compound.

Example 14: Diethyl 3,3-difluoropentanedioate. To a solution of 4.7 mmol of the product of Example 13 in 2 mL of methylene chloride, add a catalytic amount (spatula tip) of $SbCl_3$ and 6.6 mmol of bis(2-methoxyethyl)aminosulfur trifluoride. Stir for 6 h at room temperature, then dilute with about 15 mL of methylene chloride and pour onto 20 mL of saturated sodium bicarbonate. After gas evolution ceases, separate layers and extract the aqueous portion twice more with methylene chloride. Combine organic layers, wash with half-saturated brine, and dry over $MgSO_4$. Concentrate in vacuo and purify the residue by silica gel chromatography using ethyl acetate/hexanes eluant to yield the title compound.

Example 15: 1-Benzyl-4,4-difluoropiperidine-2,6-dione. React an 8.1 mmol portion of the product of Example 14 with benzylamine using the general procedure set forth in Example 8, and purify by silica gel chromatography using ethyl acetate/hexane as eluant to yield the title compound.

Example 16: 1-Benzyl-4,4-difluoro-2,2,6,6,-tetradeuteropiperidine. Reduce 6.2 mmol of the product of Example 15 with lithium aluminum deuteride using the general procedure set forth in Example 1, and purify by silica gel chromatography using methylene chloride/methanol/saturated $NH_4OH$ as eluant to yield the title compound.

Example 17: 4,4-Difluoro-2,2,6,6,-tetradeuteropiperidine hydrochloride. Debenzylate 4.9 mmol of the product of Example 16 using the general procedure set forth in Example 2. Following removal of solvent, dissolve the residue in 20 mL of diisopropyl ether and cool in an ice/water bath under argon. Treat with a slow stream of gaseous HCl to form the salt. After standing for 1 h, filter, washing with diisopropyl ether, and dry in vacuo to yield the title compound.

Example 18: 4,4-Difluoro-2,2,6,6,-tetradeutero-1-nitrosopiperidine. Nitrosylate 3.8 mmol of the product of Example 17 using the general procedure set forth in Example 4 to yield the title compound, which is used directly in subsequent reactions.

Example 19: 4,4-Difluoro-2,2,6,6,-tetradeuteropiperidin-1-amine hydrochloride. Reduce the entire yield of the product of Example 18, except for a ca. 2 mg retained sample, according to the general procedure set forth in Example 5 to yield the title compound.

Example 20: Diethyl 2,2'-(1,3-dithiane-2,2-diyl)bis(2,2-difluoroacetate). Dissolve 12.1 mmol of the product of Example 6 in 50 mL of methylene chloride and cool in an ice/water bath under argon. Add 6 g of powdered activated 3A molecular sieves, 18.2 mmol of 1,3-propanedithiol, and then 2.4 mmol of $BF_3Et_2O$. Stir for 18 h in the cold, then filter the reaction, washing with ether. Add 100 mL of ether and wash with saturated sodium bicarbonate, water, and brine, and dry over $MgSO_4$. Purify by silica gel chromatography using ether/hexane as eluant to yield the title compound.

Example 21: 9-Benzyl-7,7,11,11-tetrafluoro-1,5-dithia-9-azaspiro[5.5]undecane-8,10-dione. React 7.2 mmol of the product of Example 20 with benzylamine using the general procedure set forth in Example 8, and purify by silica gel chromatography using ethyl acetate/hexane as eluant to yield the title compound.

Example 22: 9-Benzyl-8,8,10,10-tetradeutero-7,7,11,11-tetrafluoro-1,5-dithia-9-azaspiro[5.5]undecane. Reduce a 4.2 mmol portion of the product of Example 21 with lithium aluminum deuteride using the general procedure set forth in Example 1, and purify using silica gel chromatography using methylene chloride/methanol/saturated $NH_4OH$ as eluant to yield the title compound.

Example 23: 1-Benzyl-2,2,6,6-tetradeutero-3,3,5,5-tetrafluoropiperidine. Treat a solution of 2.7 mmol of the product of Example 22 in 15 mL of ethanol under argon with an excess amount of an ethanol suspension of Raney nickel. Stir for 30 min at room temperature, then filter under argon. Purify the residue by silica gel chromatography using methylene chloride/methanol/saturated $NH_4OH$ as eluant to yield the title compound.

Example 24: 2,2,6,6-Tetradeutero-3,3,5,5-tetrafluoropiperidine hydrochloride. Debenzylate 2.1 mmol of the product of Example 23 using the general procedure set forth in Example 2 and form the hydrochloride salt in diisopropyl ether to yield the title compound.

Example 25: 2,2,6,6-Tetradeutero-3,3,5,5-tetrafluoro-1-nitrosopiperidine. Nitrosylate 1.6 mmol of the product of Example 24 using the general procedure set forth in Example 4 to yield the title compound, which is used directly in subsequent reactions.

Example 26: 2,2,6,6-Tetradeutero-3,3,5,5-tetrafluoropiperidin-1-amine hydrochloride. Reduce the entire yield of the product of Example 25, except for a ca. 1 mg retained sample, according to the general procedure set forth in Example 5 to yield the title compound.

Example 27: 4,4-Difluoro-1-nitrosopiperidine. Nitrosylate 11.2 mmol of 4,4-difluoropiperidine hydrochloride using the general procedure set forth in Example 4 to yield the title compound, which is used directly in subsequent reactions.

Example 28: 4,4-Difluoropiperidin-1-amine hydrochloride. Reduce the entire yield of the product of Example 27 except for a ca. 15 mg retained sample, according to the general procedure set forth in Example 5 to yield the title compound.

Example 29: 9-Benzyl-7,7,11,11-tetrafluoro-1,5-dithia-9-azaspiro[5.5]undecane. React 4.9 mmol of the product of Example 21 with lithium aluminum hydride, using the general procedure set forth in Example 1. Purify by silica gel chromatography using methylene chloride/methanol/saturated $NH_4OH$ as eluant to yield the title compound.

Example 30: 1-Benzyl-3,3,5,5-tetrafluoropiperidine. React 4.0 mmol of the product of Example 29 with Raney nickel according to the general procedure set forth in Example 23 and purify by silica gel chromatography using methylene chloride/methanol/saturated $NH_4OH$ as eluant to yield the title compound.

Example 31: 3,3,5,5-Tetrafluoropiperidine hydrochloride. Debenzylate 2.8 mmol of the product of Example 30 using the general procedure set forth in Example 2 and form the hydrochloride salt in diisopropyl ether to yield the title compound.

Example 32: 3,3,5,5-Tetrafluoro-1-nitrosopiperidine. Nitrosylate 2.3 mmol of the product of Example 31 using the general procedure set forth in Example 4 to yield the title compound, which is used directly in subsequent reactions.

Example 33: 3,3,5,5-Tetrafluoropiperidin-1-amine hydrochloride. Reduce the entire yield of the product of Example 32, except for a ca. 2 mg retained sample, according to the general procedure set forth in Example 5 to yield the title compound.

Example 34: 3,3,3-trideutero-N-methoxy-N-methylpropanamide. To a cold (ice/water bath) solution of 61.9 mol of 3,3,3-trideuteropropionic acid in 140 mL of methylene chloride, add 65 mmol of N-methyl-O-methyl hydroxylamine hydrochloride and 130 mmol of diisopropylethylamine, followed by 65 mmol of (benzotriazol-1-yloxy)tris(dimethylamino)phosphonium hexafluorophosphate. Stir for 17 h, warming slowly to room temperature. Concentrate to about half volume in vacuo and partition the residue between 2 volumes of ether and 1 volume of half-saturated brine. Wash the organic layer with 1N HCl, saturated sodium bicarbonate solution, and brine, and dry over $MgSO_4$. Concentrate in vacuo and purify the residue by silica gel chromatography using ethyl acetate/hexanes eluant to yield the title compound.

Example 35: 1-(4-Chlorophenyl)-3,3,3-trideuteropropan-1-one. Cool a solution of 37 mmol of 1-bromo-4-chlorobenzene in 160 mL of dry THF under argon in a $CO_2$/acetone bath. Add 37 mmol of 1N n-butyllithium dropwise during about 1 h. Stir for an additional 0.25 h to form solution 1. In a separate vessel, dissolve a 37 mmol portion of the product of Example 34 in 50 mL of dry THF and cool ($CO_2$/acetone) under argon to form solution 2. Transfer solution 1 into solution 2 by cannulation. Stir for 1 h, then remove the cold bath and stir for an additional 2 h, warming slowly to room temperature. Quench the reaction by careful addition of about 1 mL of acetic acid and concentrate in vacuo. Partition the residue between ether and water, then wash the ether layer with 10% $KHSO_4$ solution, saturated $NaHCO_3$, and brine, dry over $MgSO_4$, and concentrate in vacuo. Purify the residue by silica gel chromatography using ethyl acetate/hexanes eluant to yield the title compound.

Example 36: Lithium 4-(4-chlorophenyl)-1-ethoxy-3-trideuteromethyl-1,4-dioxobut-2-en-2-olate. To a cold (acetone/$CO_2$ bath) solution of 16 mmol of lithium bis-(trimethylsilyl)amide (1M in hexane) and 80 mL of ether under argon, add a cold (acetone/$CO_2$ bath) solution of the product of Example 35 (16 mmol) in 20 mL of ether during about 5 min. Stir for 45 min in the cold, then add 17.6 nunol of diethyl oxalate dropwise during about 2 min. Remove the cold bath and stir for about 18 h., filter under argon, and wash with additional ether. Dry the filtrate in vacuo to yield the title compound which is used without purification.

Example 37: Ethyl 5-(4-chlorophenyl)-1-(2,4-dichlorophenyl)-4-trideuteromethyl-1H-pyrazole-3-carboxylate. Dissolve 10.2 mmol of the product of Example 36 in 35 mL of ethanol. Add 11.22 mmol of 2,4-dichlorophenylhydrazine hydrochloride. Stir for 19 h at room temperature, filter the precipitate and wash with ethanol and ether and dry in vacuo. Suspend the resulting solid in 25 mL of acetic acid and heat under reflux for 21 h, then partition the reaction mixture between 100 mL of water and 3×80 mL of ethyl acetate. Combine the organic layers and wash with saturated sodium bicarbonate and brine, dry over $MgSO_4$, and concentrate in vacuo. Purify the residue by silica gel chromatography using ethyl acetate/hexanes eluant to yield the title compound.

Example 38: 5-(4-chlorophenyl)-1-(2,4-dichlorophenyl)-4-(trideuteromethyl)-1H-pyrazole-3-carboxylic acid. Dissolve 6.0 mmol of the product of Example 37 in 25 mL of methanol and add a solution of 12 mmol of KOH in 25 mL of water. Heat under reflux for 2.5 h. Cool to room temperature and treat with 120 mL of cold water. Adjust pH of the mixture to about 1 with 1N HCl. Filter the resulting solid, wash the filter cake with water, and dry in vacuo.

Example 39: 5-(4-chlorophenyl)-1-(2,4-dichlorophenyl)-N-(2,2,6,6-tetradeuteropiperidin-1-yl)-4-(trideuteromethyl)-1H-pyrazole-3-carboxamide hydrochloride. Suspend 1.2 mmol of the product of Example 38 in 4 mL of toluene. Add 3.6 mmol of thionyl chloride and heat under reflux for 3 h. Evaporate in vacuo and dissolve the residue in 6 mL of toluene. Evaporate again to yield the crude acid chloride. Dissolve this material in 6 mL of methylene chloride and add to a cold (ice/water bath) solution of 1.67 mmol of the product of example 3 and 3.67 mmol of diisopropylethylamine in 10 mL of methylene chloride. Stir for 2 h, remove the cold bath and stir an additional 2 h. Wash the reaction mixture with water and extract the aqueous layer with additional methylene chloride. Combine organic layers and wash with half-saturated brine, dry over $MgSO_4$ and concentrate in vacuo. Purify the major product by silica gel chromatography using ethyl acetate/hexanes eluant. Dissolve the isolated free base product in 10 mL of ether and treat with dropwise with 0.29 mL of 4.2N HCl in dioxane. Filter the precipitate, wash with ether and dry in vacuo to yield the title compound.

Example 40: 5-(4-chlorophenyl)-N-(2,2,3,3,4,4,5,5,6,6-decadeuteropiperidin-1-yl)-1-(2,4-dichlorophenyl)-4-(trideuteromethyl)-1H-pyrazole-3-carboxamide hydrochloride. Form the acid chloride from 3.1 mmol of the product of Example 38 and react it with 4.34 mmol of the product of Example 5, using the general procedure set forth in Example 39, to yield the title compound as a white solid.

Example 41: 5-(4-chlorophenyl)-1-(2,4-dichlorophenyl)-4-methyl-N-(2,2,6,6-tetradeuteropiperidin-1-yl)-1H-pyrazole-3-carboxamide hydrochloride. Form the acid chloride from 1.72 mmol of 5-(4-chlorophenyl)-1-(2,4-dichlorophenyl)-4-methyl-1H-pyrazole-3-carboxylic acid (e.g. Barth F et al., U.S. Pat. No. 5,624,941 to Sanofi) and react it with 2.4 mmol of the product of Example 3, using the general procedure set forth in Example 39, to yield the title compound as a white solid.

Example 42: 5-(4-chlorophenyl)-N-(2,2,3,3,4,4,5,5,6,6-decadeuteropiperidin-1-yl)-1-(2,4-dichlorophenyl)-4-methyl-1H-pyrazole-3-carboxamide hydrochloride. Form the acid chloride from 9.21 mmol of 5-(4-chlorophenyl)-1-(2,4-dichlorophenyl)-4-methyl-1H-pyrazole-3-carboxylic acid and react it with 12.9 mmol of the product of Example 5 using the general procedure set forth in Example 39, to yield the title compound as a white solid.

Example 43: 5-(4-Chlorophenyl)-1-(2,4-dichlorophenyl)-N-(3,3,4,4,5,5-hexafluoro-2,2,6,6,-tetradeuteropiperidin-1-yl)-4-methyl-1H-pyrazole-3-carboxamide hydrochloride. Form the acid chloride from 0.36 mmol of 5-(4-chlorophenyl)-1-(2,4-dichlorophenyl)-4-methyl-1H-pyrazole-3-carboxylic acid and react it with 0.50 mmol of the product of Example 12 using the general procedure set forth in Example 39, to yield the title compound as a white solid.

Example 44: 5-(4-Chlorophenyl)-1-(2,4-dichlorophenyl)-N-(4,4-difluoro-2,2,6,6,-tetradeuteropiperidin-1-yl)-4-methyl-1H-pyrazole-3-carboxamide hydrochloride. Form the acid chloride from 1.7 mmol of 5-(4-chlorophenyl)-1-(2,4-dichlorophenyl)-4-methyl-1H-pyrazole-3-carboxylic acid and react it with 1.2 mmol of the product of Example 19 using the general procedure set forth in Example 39, to yield the title compound as a white solid.

Example 45: 5-(4-Chlorophenyl)-1-(2,4-dichlorophenyl)-4-methyl-N-(2,2,6,6-tetradeutero-3,3,5,5-tetrafluoropiperidin-1-yl)-1H-pyrazole-3-carboxamide hydrochloride. Form the acid chloride from 3.4 mmol of 5-(4-chlorophenyl)-1-(2,4-dichlorophenyl)-4-methyl-1H-pyrazole-3-carboxylic acid and react it with 2.4 mmol of the product of Example 26 using the general procedure set forth in Example 39, to yield the title compound as a white solid.

Example 46: 5-(4-Chlorophenyl)-1-(2,4-dichlorophenyl)-N-(4,4-difluoropiperidin-1-yl)-4-methyl-1H-pyrazole-3-carboxamide hydrochloride. Form the acid chloride from 3.6 mmol of 5-(4-chlorophenyl)-1-(2,4-dichlorophenyl)-4-methyl-1H-pyrazole-3-carboxylic acid and react it with 2.6 mmol of the product of Example 28 using the general procedure set forth in Example 39, to yield the title compound as a white solid.

Example 47: 5-(4-Chlorophenyl)-1-(2,4-dichlorophenyl)-N-(4,4-difluoropiperidin-1-yl)-4-(trideuteromethyl)-1H-pyrazole-3-carboxamide hydrochloride. Form the acid chloride from 4.3 mmol of the product of Example 38 and react it with 3.1 mmol of the product of Example 28, using the general procedure set forth in Example 39, to yield the title compound as a white solid.

Example 48: 5-(4-Chlorophenyl)-1-(2,4-dichlorophenyl)-4-methyl-N-(3,3,5,5-tetrafluoropiperidin-1-yl)-1H-pyrazole-3-carboxamide hydrochloride. Form the acid chloride from 2.0 mmol of 5-(4-chlorophenyl)-1-(2,4-dichlorophenyl)-4-methyl-1H-pyrazole-3-carboxylic acid and react it with 1.4 mmol of the product of Example 33 using the general procedure set forth in Example 39, to yield the title compound as a white solid.

Example 49: 5-(4-Chlorophenyl)-1-(2,4-dichlorophenyl)-N-(3,3,5,5-tetrafluoropiperidin-1-yl)-4-(trideuteromethyl)-1H-pyrazole-3-carboxamide hydrochloride. Form the acid chloride from 1.8 mmol of the product of Example 38 and react it with 1.3 mmol of the product of Example 33, using the general procedure set forth in Example 39, to yield the title compound as a white solid.

Example 50: 4-(tert-Butyldimethylsilyloxy)piperidine-2,6-dione. Dissolve 4.1 mmol of 4-(tert-butyldimethylsilyloxy)dihydro-2H-pyran-2,6(3H)-dione (Nagao Y et al., Chem. Lett. 1990 9: 1503) in 10 mL of dioxane in a pressure tube. Cool in an ice/water bath, add 15 mL of saturated ammonium hydroxide and treat with gaseous ammonia via bubbler for about 10 min. Cap the pressure tube and heat in a 100° C. oil bath for 17 h. Cool the mixture and concentrate in vacuo. Purify the residue by silica gel chromatography using ethyl acetate/hexanes eluant to yield the title compound.

Example 51: 4-(tert-Butyldimethylsilyloxy)-2,2,6,6-tetradeuteropiperidine. Dissolve a 3.1 mmol sample of the product of Example 50 in 20 mL of methylene chloride. Treat with 4.6 mmol of N,O-bis(trimethylsilyl)trifluoroacetamide and stir for 1 h at room temperature. Concentrate in vacuo, dissolve the residue in 15 mL of toluene and concentrate to yield the N-trimethylsilyl imide. Dissolve this material in 10 mL of THF and reduce with LiAlD$_4$ according to the general procedure set forth in Example 1.

Example 52: 2,2,6,6-Tetradeutero-1-nitrosopiperidin-4-ol. Using the general procedure set forth in Example 4, N-nitrosylate a 12.9 mmol sample of the product of Example 51 to yield the title compound.

Example 53: 4-Fluoro-2,2,6,6-tetradeutero-1-nitrosopiperidine. Dissolve a 2.3 mmol sample of the product of Example 52 in 5 mL of methylene chloride and add it dropwise during 5 min to a cold (ice/methanol bath) solution of 2.3 mmol of diethylaminosulfur trifluoride in 5 mL of methylene chloride. Stir the solution for 10 min, then remove the cold bath and stir for 1 h at room temperature. Dilute the mixture with 25 mL of ether and wash sequentially with saturated NaHCO$_3$ solution and brine, then dry over MgSO$_4$ and concentrate in vacuo. Purify the residue by silica gel chromatography using ethyl acetate/hexanes eluant to yield the title compound.

Example 54: 4-Fluoro-2,2,6,6-tetradeuteropiperidin-1-amine hydrochloride. Reduce a 6.3 mmol portion of the product of Example 53 with LiAlH$_4$ and form the hydrochloride salt using the general procedure outlined in Example 5 to yield the title compound.

Example 55: 5-(4-Bromophenyl)-1-(2,4-dichlorophenyl)-4-ethyl-N-(2,2,6,6-tetradeuteropiperidin-1-yl)-1H-pyrazole-3-carboxamide. Add a 1.5 mmol sample of 5-(4-bromophenyl)-1-(2,4-dichlorophenyl)-4-ethyl-1H-pyrazole-3-carbonyl chloride (Barth F et al., US Patent Application 20040039024, Sanofi-Synthelabo Applicant) under argon to a cold (ice/water) solution 1.5 mmol of the product of Example 3 and 3.3 mmol of diisopropylethylamine in 10 mL of methylene chloride. Add a catalytic amount of 4-dimethylaminopyridine (spatula tip) and stir for 15 min. Remove the ice bath and stir for 16 h at room temperature. Dilute the reaction mixture with 20 mL of ether and wash sequentially with water, saturated NaHCO$_3$ solution, and brine. Dry over MgSO$_4$, concentrate in vacuo and purify the residue by silica gel chromatography using ethyl acetate/toluene eluant to yield the title compound.

Example 56: 5-(4-Bromophenyl)-N-(4-fluoro-2,2,6,6-tetradeuteropiperidin-1-yl)-1-(2,4-dichlorophenyl)-4-ethyl-1H-pyrazole-3-carboxamide. React a 2.1 mmol sample of 5-(4-bromophenyl)-1-(2,4-dichlorophenyl)-4-ethyl-1H-pyrazole-3-carbonyl chloride with an equimolar amount of the product of Example 54 using the general procedure set forth in Example 55 to yield, following by silica gel chromatography using ethyl acetate/toluene eluant, the title compound.

Example 56-A: 5-(4-Bromophenyl)-N-(4,4-difluoro-2,2,6,6-tetradeuteropiperidin-1-yl)-1-(2,4-dichlorophenyl)-4-ethyl-1H-pyrazole-3-carboxamide. React a 2.1 mmol sample of 5-(4-bromophenyl)-1-(2,4-dichlorophenyl)-4-ethyl-1H-pyrazole-3-carbonyl chloride with an equimolar amount of the product of Example 19 using the general procedure set forth in Example 55 to yield, following by silica gel chromatography using ethyl acetate/toluene eluant, the title compound.

Example 57: Ethyl 5-(4-bromophenyl)-1-(2,4-dichlorophenyl)-4-(2,2,2-trideuteroethyl)-1H-pyrazole-3-carboxylate. Cool a suspension of 2.2 mmol CuBr in 10 mL of ether, under argon, in a −20° C. bath and add dropwise during 5 min 4.5 mL of 0.5 M methyl-d$_3$-lithium. Continue stirring for about 10 min as the mixture forms a clear solution, then cool in a −78° C. bath and add dropwise during 20 min a solution of 2.0 mmol of ethyl 4-(bromomethyl)-5-(4-bromophenyl)-1-(2,4-dichlorophenyl)-1H-pyrazole-3-carboxylate (Barth F et al., US Patent Application 20040039024, Sanofi-Synthelabo Applicant). Stir the resulting solution for an additional 0.5 h in the cold, remove the cold bath and stir for an additional 2 h. Quench the reaction with saturated NH$_4$Cl solution. Dilute with additional ether, separate the organic layer, and wash sequentially with water and brine. Dry over MgSO$_4$, concentrate in vacuo and purify by silica gel chromatography using ethyl acetate/toluene eluant, to yield the title compound.

Example 58: 5-(4-Bromophenyl)-1-(2,4-dichlorophenyl)-4-ethyl-1H-pyrazole-3-carboxylic acid. Hydrolyze a 1.3 mmol sample of the product of Example 57 according to the general procedure set forth in Example 38 to yield the title compound.

Example 59: 5-(4-bromophenyl)-1-(2,4-dichlorophenyl)-N-(piperidin-1-yl)-4-(2,2,2-trideuteroethyl)-1H-pyrazole-3-carboxamide. Form the acid chloride of a 1.6 mmol portion of the product of Example 58 and react it with piperidin-1-amine hydrochloride according to the general procedure set forth in Example 39 to yield the title compound.

Example 60: 5-(4-bromophenyl)-1-(2,4-dichlorophenyl)-N-(4,4-difluoropiperidin-1-yl)-4-(2,2,2-trideuteroethyl)-1H-pyrazole-3-carboxamide. Form the acid chloride of a 0.9 mmol portion of the product of Example 58 and react it with 4,4-difluoropiperidin-1-amine hydrochloride according to the general procedure set forth in Example 39 to yield the title compound.

Example 61: 5-(4-Bromophenyl)-1-(2,4-dichlorophenyl)-N-(2,2,6,6-tetradeuteropiperidin-1-yl)-4-(2,2,2-trideuteroethyl)-1H-pyrazole-3-carboxamide. Form the acid chloride of a 1.2 mmol portion of the product of Example 58 and react it with the product of Example 3 according to the general procedure set forth in Example 39 to yield the title compound.

Example 62: 5-(4-Bromophenyl)-1-(2,4-dichlorophenyl)-N-(4-fluoro-2,2,6,6-tetradeuteropiperidin-1-yl)-4-(2,2,2-trideuteroethyl)-1H-pyrazole-3-carboxamide. Form the acid chloride of a 1.2 mmol portion of the product of Example 58 and react it with the product of Example 54 according to the general procedure set forth in Example 39 to yield the title compound.

Example 63: 5-(4-Bromophenyl)-1-(2,4-dichlorophenyl)-N-(4,4-difluoro-2,2,6,6-tetradeuteropiperidin-1-yl)-4-(2,2,2-trideuteroethyl)-1H-pyrazole-3-carboxamide. Form the acid chloride of a 1.2 mmol portion of the product of Example 58 and react it with the product of Example 19 according to the general procedure set forth in Example 39 to yield the title compound.

Example 64: $CB_1$ and $CB_2$ binding screens. Test compounds are assayed for concentration at which they displace WIN 55212-2 (5 μM) in cell lines expressing, respectively, recombinant human $CB_1$ and $CB_2$ receptors (see Rinaldi-Carmona M et al., J. Pharmacol. Exp. Ther. 1996 278: 871 and Munro S et al., Nature 1993 365: 61). Each compound tested displays sub-micromolar binding potency at the $CB_1$ receptor and substantial selectivity for $CB_1$ versus $CB_2$.

Example 65: $CB_1$ receptor antagonist activity. Test compounds are assayed for concentration at which they inhibit [$^{35}$S]GTPγS binding in recombinant cells expressing human $CB_1$ receptors stimulated by anandamide (see Gonsiorek W et. al., Mol. Pharmacol. 2000 57: 1045). Each of compound tested effectively antagonizes the $CB_1$ receptor at sub-micromolar concentrations.

Example 66: Stability in human liver microsomes. Half-life of test compounds at 1 μM in the presence of human liver S9 fraction, standardized to 1 mg/mL total protein, is measured by disappearance of the parent mass ion using HPLC/MS detection (see Singh R et al., 1996 Rapid Commun. Mass Spectrom. 10: 1019). Representative compounds from classes 4-9 and compounds containing both fluorine and deuterium from the classes in table I display altered oxidative metabolism and similar or greater half lives than Compound 1.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Another embodiment is a compound of any of the formulae herein made by a process delineated herein, including the processes exemplified in the schemes and examples herein. Another aspect of the invention is a compound of any of the formulae herein for use in the treatment or prevention in a subject of a disease, disorder or symptom thereof delineated herein. Another aspect of the invention is use of a compound of any of the formulae herein in the manufacture of a medicament for treatment or prevention in a subject of a disease, disorder or symptom thereof delineated herein.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound selected from a compound of Formula II:

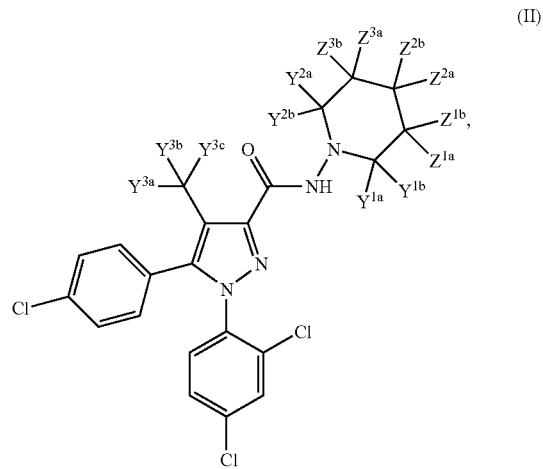

(II)

or a pharmaceutically acceptable salt thereof; wherein:
each $Y^1$, each $Y^2$, and each Z is deuterium; and
each $Y^3$ is independently selected from deuterium or hydrogen.

2. The compound according to claim 1, wherein $Y^{3a}$, $Y^{3b}$, and $Y^{3c}$ are simultaneously deuterium.

3. The compound according to claim 1, wherein said compound is selected from a compound class set forth in the table below, wherein D is deuterium; any undesignated Y or Z is hydrogen; and any hydrogen that is not Y or Z is optionally replaced by deuterium;

| Compound Class | $Y^{1a}$ | $Y^{1b}$ | $Y^{2a}$ | $Y^{2b}$ | $Y^{3a}$ | $Y^{3b}$ | $Y^{3c}$ | $Z^{1a}$ | $Z^{1b}$ | $Z^{2a}$ | $Z^{2b}$ | $Z^{3a}$ | $Z^{3b}$ | $Y^{4a}$ | $Y^{4b}$ | Formula |
|---|---|---|---|---|---|---|---|---|---|---|---|---|---|---|---|---|
| 4 | | | | | | | | | | | | | | | | |
| 9 | D | D | D | D | | | | D | D | D | D | D | D | | | II |
| 10 | D | D | D | D | D | D | D | D | D | D | D | D | D | | | II |

4. The compound according to claim 3, wherein each hydrogen atom that is not Y or Z is present at its naturally occurring isotopic abundance.

5. A mixture consisting of:
   a. a compound of Formula II according to claim 1 wherein each $Y^1$, each $Y^2$ and each Z is deuterium; and each $Y^3$ is independently selected from the group consisting of deuterium and hydrogen; and
   b. lighter isotopologues of said compound of Formula II, wherein at least 50% of said mixture is said compound of Formula II.

6. A mixture consisting of:
   c. a compound of Formula II according to claim 1 wherein each $Y^1$, each $Y^2$ and each Z is deuterium; and each $Y^3$ is independently selected from the group consisting of deuterium and hydrogen; and
   d. lighter isotopologues of said compound of Formula II, wherein at least 50% of the compounds in said mixture comprise an isotope at each position indicated as being occupied by an isotope in a chemical formula of said compound of Formula II.

7. A pharmaceutical composition comprising a compound according to claim 1 or a pharmaceutically acceptable salt of said compound; and an acceptable carrier.

8. The pharmaceutical composition according to claim 7, further comprising an effective amount of a second therapeutic agent, wherein said second therapeutic agent is useful for treating a condition in a patient selected from obesity, diabetes, and coronary artery disease.

9. The composition according to claim 8, wherein said second therapeutic agent is selected from a norepinephrine transporter inhibitor, a ghrelin antagonist, a H3 antagonist/inverse agonist, a melanin-concentrating hormone 1 receptor antagonist, a melanin-concentrating hormone 2 receptor agonist/antagonist, a neuropeptide Y1 antagonist, a neuropeptide Y2 agonist, a neuropeptide Y4 agonist, a neuropeptide Y5 antagonist, a metabotropic glutamate subtype 5 receptor antagonist, leptin, a leptin agonist/modulator, a leptin derivative, an opioid antagonist, an orexin antagonist, a cholecystokinin-A agonist, a serotonin reuptake inhibitor, ciliary neurotrophic factor (CNTF), a CNTF agonist/modulator, a CNTF derivative, a 5-hydroxytryptamine 2c agonist, a melanocortin 4 receptor agonist, a monoamine reuptake inhibitor, a serotonin reuptake inhibitor, a glucagon-like-peptide-1 agonist, topiramate, phytopharm compound 57, a COX-2 inhibitor, a PPARα agonist, an aldosterone antagonist; a lipase inhibitor; or a pharmaceutically acceptable salt of any of the foregoing agents.

* * * * *